(12) United States Patent
Hildebrandt et al.

(10) Patent No.: US 7,253,271 B2
(45) Date of Patent: Aug. 7, 2007

(54) BSND NUCLEIC ACIDS AND PROTEINS

(75) Inventors: Friedhelm Hildebrandt, Ann Arbor, MI (US); Thomas J. Jentsch, Hamburg (DE)

(73) Assignee: Regents of the University of Michigan, Ann Arbor, MI (US)

( * ) Notice: Subject to any disclaimer, the term of this patent is extended or adjusted under 35 U.S.C. 154(b) by 646 days.

(21) Appl. No.: 10/273,476

(22) Filed: Oct. 18, 2002

(65) Prior Publication Data

US 2004/0023234 A1 Feb. 5, 2004

Related U.S. Application Data

(60) Provisional application No. 60/333,637, filed on Nov. 26, 2001, provisional application No. 60/345,002, filed on Oct. 19, 2001.

(51) Int. Cl.
*C07H 21/04* (2006.01)
*C12N 15/63* (2006.01)
*C07K 5/00* (2006.01)

(52) U.S. Cl. .................. 536/23.1; 435/320.1; 530/350

(58) Field of Classification Search ............... 536/23.1; 435/6, 320.1; 530/350
See application file for complete search history.

(56) References Cited

U.S. PATENT DOCUMENTS 5,763,184 A 6/1998 Reynolds et al. .............. 435/5

FOREIGN PATENT DOCUMENTS

WO WO 200154477 A2 * 8/2001

OTHER PUBLICATIONS

Brennan et al. Linkage of infantile Bartter syndrome with sensorineural deafness to chromosome 1p. Am J. Hum. Genet., vol. 62, p. 355-361, 1998.*
Vollmer et al. Antenatal Bartter syndrome with sensorineural deafness: refienment of teh locus on chromosome 1p31. Nephrol Dial Transplant, vol. 15, p. 970-974, 2000.*
Vollmer et al., Nephrol. Dial. Transplant, 15:970-974 (1998).
Jeck et al., Pediatrics, 108:E5 (2001).
Lander et al., Science 236:1567-1570 (1987).
Brennan et al., Am. J. Hum. Genet. 62:355-361 (1998).
Igarashi et al., Am. J. Physiol. 269:F405-F418 (1995)).

Kaplan et al., Kidney Int., 49:40-47(1996). Not submitted at this time.
Yoshikawa et al., Am. J. Physiol. 276:F552-F558 (1999).
Kobayashi et al., J. Am. Soc. Nephrol. 12:1327-1334 (2001).
Kubisch et al., Cell 96:437-446 (1999).
Tyson et al., Hum. Mol. Genetics 6:2179-2185 (1997).
Schulze-Bahr et al., Nature Genetics 17:267-268 (1997). Not submitted at this time.
Petit et al., Nature Genetics 14:385-391 (1996). Not submitted at this time.
Steel, et al., Nature Genetics 27:143-149 (2001).
Delpire et al., Nature Genetics 22:192-195 (1999).
Nicolas et al., Hear. Res. 153:132-145 (2001).Not submitted at this time.
Simon et al., Nature Genetics 17:171-178 (1997). Not submitted at this time.
Vandewalle et al., Am. J. Physiol. 272:F678-F688 (1997).
Uchida et al., J. Clin. Invest. 95:104-113 (1995).
Matsumura et al., Nature Genetics 21:95-98 (1999).
Waldegger et al., J. Biol. Chem. 276:12049-12054 (2001).
Zerangue et al., Neuron 22:537-548 (1999).
Schwake et al., J. Biol. Chem. 276:12049-12054 (2001).
Jentsch et al., Pflugers Arch. Eur. J. Physiol. 437:783-795 (1999). Not submitted at this time.
Birkenhager et al., Nature Genetics 29:310-314 (2001).
Staub et al., EMBO J. 15:2371-2380 (1996).
Schild et al., EMBO J. 15:2381-2387 (1996).
Staub et al., EMBO J. 16:6325-6336 (1997).
Konrad et al., J. Am. Soc. Nephrol. 11:1449-1459 (2000).
Nielson et al., Proc. Natl. Acad. Sci. USA 90:11663-11667 (1993).
Ando et al., Neurosci. Lett. 284:171-174 (2000).
Dixon et al., Hum. Mol. Genet. 8:1579-1584 (1999).
Neyroud et al., Nature Genetics 15:186-189 (1997). Not submitted at this time.
Schulze-Bahr et al., Nature Genetics 17:267-268 (1997).
Birkenhager et al., "Mutation of BSND causes Bartter syndrome with sensorineural deafness and kidney failure," Nature Genetics 29:310-314 (2001).
Kaplan et al., Kidney Int., 49:40-47(1996).
Petit et al., Nature Genetics 14:385-391 (1996).
Nicolas et al., Hear. Res. 153:132-145 (2001).
Simon et al., Nature Genetics 17:171-178 (1997).
Jentsch et al., Pflugers Arch. Eur. J. Physiol. 437:783-795 (1999).
Neyroud et al., Nature Genetics 15:186-189 (1997).

* cited by examiner

*Primary Examiner*—Suryaprabha Chunduru
(74) *Attorney, Agent, or Firm*—Medlen & Carroll, LLP

(57) ABSTRACT

The present invention relates to the BSND (barttin) protein and nucleic acids encoding the BSND protein. The present invention provides assays for the detection of BSND and barttin polymorphisms and mutations associated with disease states.

7 Claims, 15 Drawing Sheets

FIG. 2

| | F314 | F591 | F730 | F786 | F791 | F813 | F197 | F708 | F662 | F206 |
|---|---|---|---|---|---|---|---|---|---|---|
| p-ter | 2 2 | 3 3 | 3 3 | 2 2 | 2 2 | 3 1 | 1 2 | 2 2 | 3 3 | 1 2 |
| *D1S2661* | 4 4 | 5 2 | 2 2 | 4 4 | 4 4 | 6 5 | 3 3 | 3 3 | 2 1 | 1 2 |
| 845c20-a | 4 4 | 4 4 | 1 1 | 4 4 | 4 4 | 6 7 | 4 4 | 2 2 | 2 2 | 4 4 |
| 845c20-b | 4 4 | 4 4 | 3 3 | 4 4 | 2 2 | 2 2 | 2 2 | 6 6 | 6 6 | 6 6 |
| 277a12-a | 2 2 | 2 2 | 5 5 | 1 1 | 4 4 | 5 1 | 4 4 | 2 2 | 3 3 | 2 2 |
| 277a12-b* | 3 3 | 3 2 | 4 4 | 3 3 | 4 4 | 4 6 | 3 3 | 1 1 | 1 5 | 5 5 |
| DJ1099n-07-c | 4 4 | 4 4 | 1 1 | 4 4 | 1 1 | 3 6 | 3 3 | 2 2 | 2 2 | 2 2 |
| *D1S417* | 1 1 | 1 1 | 1 1 | 1 1 | 1 1 | 3 3 | 3 3 | 2 2 | 2 2 | 2 2 |
| *D1S2652* | 1 1 | 1 1 | 1 1 | 1 1 | 1 1 | 3 3 | 3 3 | 2 2 | 3 3 | 2 2 |
| 109i2-b** | 3 3 | 3 3 | 3 3 | 3 3 | 3 3 | 3 3 | 3 3 | 3 3 | 3 3 | 1 1 |
| 101c11-e* | 1 1 | 1 1 | 1 1 | 1 1 | 5 5 | 1 1 | 4 4 | 5 5 | 5 5 | 5 5 |
| 319f11-a | 2 2 | 2 2 | 4 4 | 4 4 | 2 2 | 4 4 | 4 4 | 5 5 | 4 4 | 4 4 |
| 633h17-g | 5 5 | 2 2 | 1 1 | 3 3 | 1 1 | 1 1 | 2 2 | 1 1 | 1 1 | 1 1 |
| *D1S475* | 2 2 | 2 2 | 2 2 | 2 2 | 2 2 | 2 2 | 2 2 | 2 2 | 1 1 | 5 5 |
| *D1S200* | 2 2 | 2 2 | 2 2 | 3 3 | 1 2 | 2 2 | 2 2 | 5 5 | 3 3 | 3 3 |
| *D1S2690* | 4 4 | 4 4 | 2 2 | 4 4 | 4 3 | 4 4 | 4 1 | 4 4 | 4 4 | 5 5 |
| cen | | | | | | | | | | 4 4 |

FIG. 7

```
SEQ: 1      GAGAGGGCAAGGAGTAAAGGTGGCTGGGTGTGGGTCCGTTGAAGCGAGCCGCCTCCAGCCCTG
            TTGAACTGGTGGGCCCAGGGACTGGAGCGGGATTGAAAGGGATCTTGCTCTCCCTTGAAG
            CCTCGAGTTGCAGCGATTTCAGTGTCTTCTCTCCCTGTGTAAGCCTGTCTGGGTGTTTAG
            GCTGAACTACAGCCACCCCCTCTCCCGGGGTGTGCAGGCCAGGGACTGGCCAGGCAGCC
SEQ: 2    1 ATGGCTGACGAGAAGACCTTCCGGATCGGCTTCATTGTGCTGGGCTTTTCCTGCTGGCC   60
            M  A  D  E  K  T  F  R  I  G  F  I  V  L  G  L  F  L  L  A
SEQ: 3    * *  *  *  *  *  *  *  *  *  *  *  *  *  *  *  *  *  *  *  S
            CTCGGTACGTTCCTCATGAGCCATGATCGGCCCCAGGTCTACGGCACCTTCTATGCCATG  120
         21 L  G  T  F  L  M  S  H  D  R  P  Q  V  Y  G  T  F  Y  A  M
            *  *  *  *  *  *  *  *  *  *  *  *  *  *  *  *  *  *  *  *
            GGCAGCGTCATGGTGATCGGGGGCATCATCTGGAGCATGTGCCAGTGCTACCCCAAGATC  180
         41 G  S  V  M  V  I  G  G  I  I  W  S  M  C  Q  C  Y  P  K  I
            *  *  *  *  *  *  *  *  V  *  *  *  *  *  *  *  *  *  *  *
            ACCTTCGTCCCTGCTGACTCTGACTTTCAAGGCATCCTCTCCCCAAAGGCCATGGGCCTG  240
         61 T  F  V  P  A  D  S  D  F  Q  G  I  L  S  P  K  A  M  G  L
            *  *  *  *  *  *  *  *  *  *  *  *  *  *  *  *  L  S  *  *
            CTGGAGAATGGGCTTGCTGCCGAGATGAAGAGCCCCAGTCCCCAGCCGCCCTATGTAAGG  300
         81 L  E  N  G  L  A  A  E  M  K  S  P  S  P  Q  P  P  Y  V  R
            *  *  A  *  *  -  S  *  V  *  -  -  *  *  *  *  *  *  *  *
            CTGTGGGAGGAAGCCGCCTATGACCAGAGCCTGCCTGACTTCAGCCACATCCAGATGAAA  360
        101 L  W  E  E  A  A  Y  D  Q  S  L  P  D  F  S  H  I  Q  M  K
            *  *  *  *  *  *  *  *  *  *  *  *  *  T  *  *  *  *  *  *
            GTCATGAGCTACAGTGAGGACCACCGCTCCTTGCTGGCCCCTGAGATGGGGCAGCCGAAG  420
        121 V  M  S  Y  S  E  D  H  R  S  L  L  A  P  E  M  G  Q  P  K
            *  *  G  *  *  *  *  P  *  P  *  *  *  *  L  -  -  -  -  *
            CTGGGAACCAGTGATGGAGGAGAAGGTGGCCCTGGCGACGTTCAGGCCTGGATGGAGGCT  480
        141 L  G  T  S  D  G  G  E  G  G  P  G  D  V  Q  A  W  M  E  A
            T  *  A  *  S  V  R  *  *  E  *  R  T  A  *  *  *  *  *  *
            GCCGTGGTCATCCACAAGGGCTCAGACGAGAGTGAAGGGGAAGACGCCTAACTCAGAGC  540
        161 A  V  V  I  H  K  G  S  D  E  S  E  G  E  R  R  L  T  Q  S
            P  *  *  V  *  R  *  *  *  *  N  *  *  *  K  S  H  S  *  *
            TGGCCCGGCCCCCTGGCCTGTCCCCAGGGCCCTGCCCCCTTGGCTTCCTTCCAAGATGAC  600
        181 W  P  G  P  L  A  C  P  Q  G  P  A  P  L  A  S  F  Q  D  D
            -  -  S  *  S  V  G  *  *  *  S  *  *  *  *  *  H  *  *  *
            CTGGACATGGACTCCAGTGAAGGCAGCAGCCCCAATGCATCTCCACATGACAGGGAGGAA  660
        201 L  D  M  D  S  S  E  G  S  S  P  N  A  S  P  H  D  R  E  E
            *  *  V  G  *  *  *  *  *  *  L  Q  P  *  *  N  R  D  *  -
            GCTTGTTCCCCACAACAGGAACCTCAGGGCTGCAGGTGCCCGCTGGACCGCTTCCAAGAC  720
        221 A  C  S  P  Q  Q  E  P  Q  G  C  R  C  P  L  D  R  F  Q  D
            -  -  P  H  R  *  V  *  W  A  S  *  G  *  *  *  *  *  S  *
            TTTGCCCTGATTGATGCCCCAACGTTGGAGGATGAGCCCCAAGAGGGGCAGCAGTGGGAA  780
        241 F  A  L  I  D  A  P  T  L  E  D  E  P  Q  E  G  Q  Q  W  E
            *  *  *  D  *  T  *  *  S  *  *  T  V  L  D  *  *  A  R  *
            ATAGCCCTGCCCAACAACTGGCAGCGGTACCCAAGGACAAAGGTGGAGGAGAAGGAGGCT  840
        261 I  A  L  P  N  N  W  Q  R  Y  P  R  T  K  V  E  E  K  E  A
            A  *  *  *  P  K  Q  *  W  S  L  *  M  *  G  *  T  V  Q  *
            TCGGACACAGGTGGGGAGGAACCTGAGAAGGAAGAGGAAGACCTGTACTATGGGCTGCCA  900
        281 S  D  T  G  G  E  E  P  E  K  E  E  D  L  Y  Y  G  L  P
            R  -  -  A  *  *  *  Q  *  *  *  *  *  *  *  *  *  *  *  *
            GATGGAGCCGGGGACCTCCTCCCGGACAAGGAGCTGGGTTTTGAGCCTGACACCCAAGGC  960
        301 D  G  A  G  D  L  L  P  D  K  E  L  G  F  E  P  D  T  Q  G
            *  S  P  *  N  P  *  *  *  *  *  *  *  *  *  *  I  *  *
            TGAGATGTTTGTGCTCCGTAGCTTTTAGTCTGGAACTGCTGCTGACCCCTGTGTGACATC 1220
        321 *
            *
            ACAGGGCCTCAGTTTCCCTATTTGCAAAATGGGATGATATGGAGGTTCAATGAGATGGTG 1280
            GCATTTTGAGAATGGTAAAGAAATACCCAGGGAGGGGATGATGCCTAAAAAAAAAAAAAA 1340
            AAAAAAAAAAAAA                                                1353
```

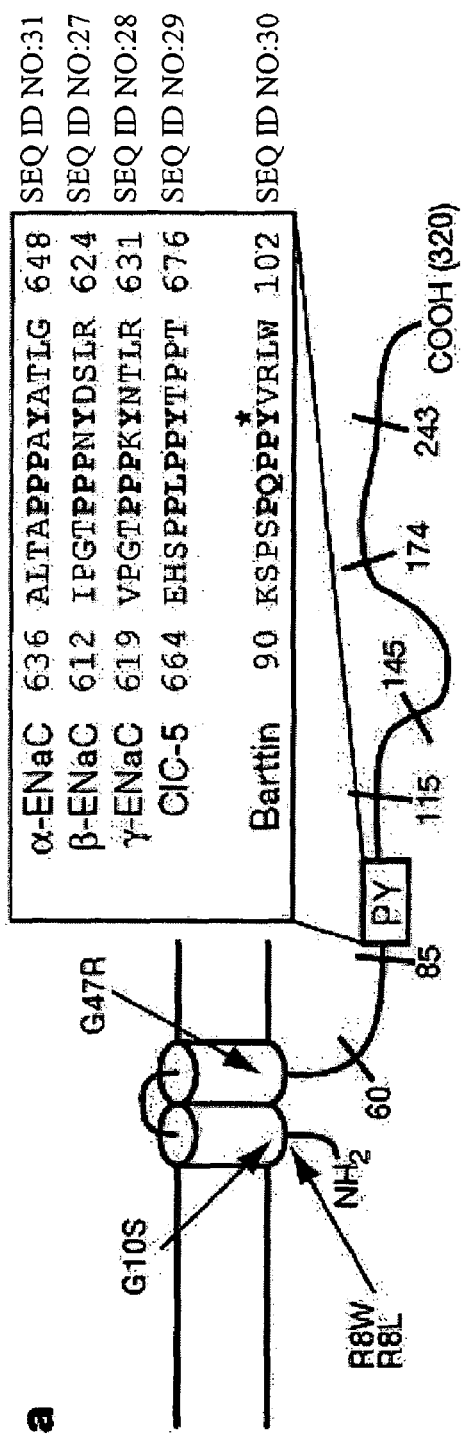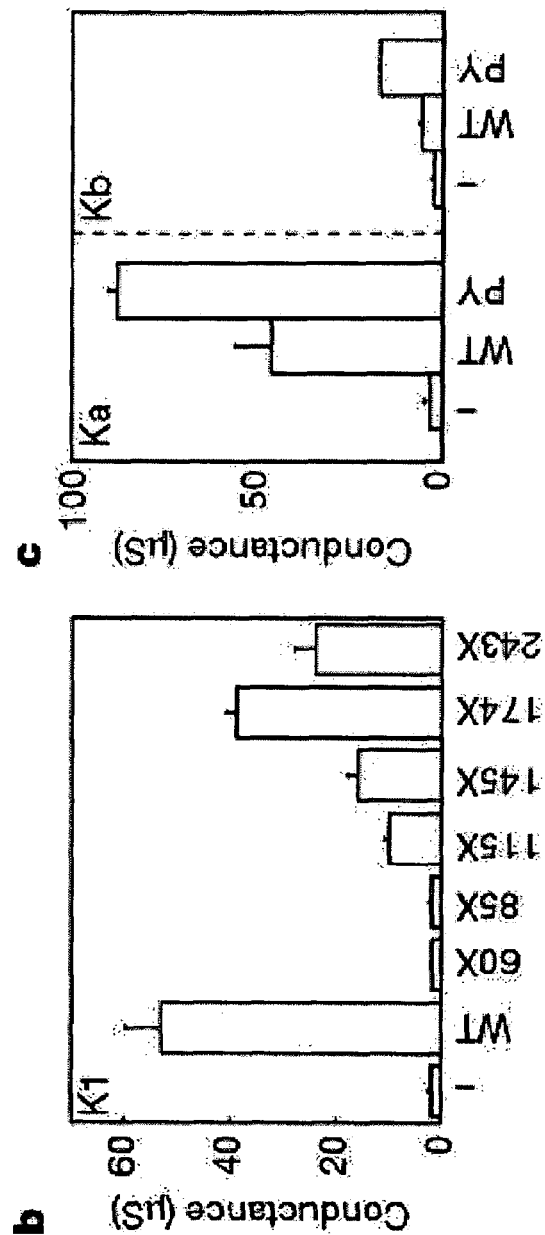
FIG. 9

BSND NUCLEIC ACIDS AND PROTEINS

This application claims priority to U.S. provisional patent application No. 60/345,002 filed on Oct. 19, 2001 with Express Mail Label ET720704983US and U.S. provisional patent application Ser. No. 60/333,637, filed Nov. 26, 2001.

FIELD OF THE INVENTION

The present invention relates to the BSND (Barttin) protein and nucleic acids encoding the BSND protein. The present invention provides assays for the detection of BSND and barttin polymorphisms and mutations associated with disease states.

BACKGROUND OF THE INVENTION

Antenatal Bartter syndrome (aBS) comprises a heterogeneous group of autosomal recessive salt-losing nephropathies (Rodriguez-Soriano, *Pediatr. Nephrol.* 12, 315-327 (1998)). Bartter's Syndrome, also known as is hypokalemic alkalosis with hypercalciuria, is a rare inherited disorder characterized by growth deficiency, potentially resulting in short stature; muscle weakness; cramps; and/or loss of potassium from the kidneys (renal potassium wasting). In some cases, affected individuals may exhibit mental retardation. Individuals with Bartter's Syndrome have a disturbance in their acid-base ratio (i.e., an accumulation of base or loss of acid) associated with a loss of potassium (hypokalemic alkalosis). Low amounts of potassium may result from overproduction of a certain hormone (aldosterone) that is essential in controlling blood pressure and regulating sodium and potassium levels (hyperaldosteronism).

There is no cure for Bartter's syndrome. The treatments consist of supplements to replace what is lost and medications to prevent urinary wasting of potassium and magnesium. In younger children growth hormone may be used to prevent the short stature and prostaglandin inhibitors to decrease the elevated prostaglandin levels. Treatments include potassium chloride supplements, magnesium supplements, spironolactone amilioride, triamterene, indomethacin, captopril, and growth hormone.

The limited prognostic information available suggests that early diagnosis and appropriate treatment of infants and young children with Classic Bartter Syndrome may improve growth and perhaps neurointellectual development. On the other hand, sustained hypokalemia and hyperreninemia can cause progressive tubulointerstitial nephritis, resulting in end-stage-renal disease (Kidney failure).

Clearly there is a great need for identification of the molecular basis of Bartter's syndrome, as well as for improved diagnostics and treatments for Bartter's syndrome.

SUMMARY OF THE INVENTION

The present invention relates to the BSND (Barttine) protein and nucleic acids encoding the BSND protein. The present invention provides assays for the detection of BSND and barttin polymorphisms and mutations associated with disease states.

Accordingly, in some embodiments, the present invention provides an isolated and purified nucleic acid comprising a sequence encoding a protein selected from the group consisting of SEQ ID NOs: 2, 5, 10, and 12. In some embodiments, the sequence is operably linked to a heterologous promoter. In some embodiments, the sequence is contained within a vector. In some embodiments, the vector is within a host cell. In some embodiments, the present invention provides a computer readable medium encoding a representation of the nucleic acid sequence.

The present invention also provides an isolated and purified nucleic acid sequence that hybridizes under conditions of low stringency to a nucleic acid selected from the group consisting of SEQ ID NOs: 1, 3, 4, 6, 7, 8, and 11. In some embodiments, the sequence is contained within a vector. In some embodiments, the vector is in a host cell. In some embodiments, the host cell is located in an organism, wherein the organism is a non-human animal.

The present invention additionally provides a protein encoded by a nucleic acid selected from the group consisting of SEQ ID NOs:1 and variants thereof that are at least 80% identical to SEQ ID NOs: 1, 3, 4, 6, 7, 8, and 11. In some embodiments, the protein is at least 90%, and preferably at least 95% identical to SEQ ID NOs: 1, 3, 4, 6, 7, 8, and 11. In some embodiments, the present invention provides a computer readable medium encoding a representation of the polypeptide sequence.

The present invention further provides a composition comprising a nucleic acid that inhibits the binding of at least a portion of a nucleic acid selected from the group consisting of SEQ ID NOs: 1, 3, 4, 6, 7, 8, and 11 to their complementary sequences. In other embodiments, the present invention provides a polynucleotide sequence comprising at least fifteen nucleotides capable of hybridizing under stringent conditions to the isolated nucleotide sequence.

In yet other embodiments, the present invention provides a composition comprising a variant barttin polypeptide, wherein the polypeptide comprises a variant of SEQ ID NO:2. In some embodiments, the variant barttin polypeptide is selected from the group consisting of SEQ ID NOs: 5, 10, and 12. In some embodiments, the presence of the variant polypeptide in a subject is indicative of Bartter's syndrome in the subject.

In still further embodiments, the present invention provides a method for detection of a variant barttin polypeptide or nucleic acid in a subject, comprising: providing a biological sample from a subject, wherein the biological sample comprises a barttin polypeptide or nucleic acid; and detecting the presence or absence of a variant barttin polypeptide or nucleic acid in the biological sample. In some embodiments, the variant barttin polypeptide is a variant of SEQ ID NO:2. In some embodiments, the variant barttin polypeptide is selected from the group consisting of SEQ ID NOs: 5, 10, and 12. In some embodiments, the variant barttin nucleic acid is a variant of SEQ ID NO:1. In some embodiments, the variant barttin nucleic acid is selected from the group consisting of SEQ ID NOs: 3, 4, 6, 7, 8, and 11. In some embodiments, the presence of the variant barttin polypeptide or nucleic acid is indicative of Bartter's syndrome in the subject. In some embodiments, the Bartter's syndrome comprises sensorineural deafness and kidney failure. In some embodiments, the biological sample is selected from the group consisting of a blood sample, a tissue sample, a urine sample, and an amniotic fluid sample. In some embodiments, the subject is selected from the group consisting of an embryo, a fetus, a newborn animal, and a young animal. In some embodiments, the animal is a human. In some embodiments, the detecting comprises differential antibody binding. In other embodiments, the detecting comprises a Western blot. In still further embodiments, the detection comprises a nucleic acid detection method selected from the group consisting of direct sequencing, polymerase chain reaction, denaturing high pressure liquid chromatography, mass spectrometry, and enzymatic detection.

The present invention further provides a kit comprising a reagent for detecting the presence or absence of a variant barttin nucleic acid or polypeptide in a biological sample. In some embodiments, the kit further comprises instruction for using the kit for detecting the presence or absence of a variant barttin nucleic acid or polypeptide in a biological sample. In some embodiments, the instructions comprise instructions required by the U.S. Food and Drug Agency for in vitro diagnostic kits. In some embodiments, the kit further comprises instructions for diagnosing Bartter's syndrome in the subject based on the presence or absence of the variant barttin nucleic acid polypeptide. In some embodiments, the Bartter's syndrome comprises sensorineural deafness and kidney failure. In some embodiments, the reagent is one or more antibodies. In other embodiments, the reagent comprises a reagent for performing a nucleic acid detection method selected from the group consisting of direct sequencing, polymerase chain reaction, denaturing high pressure liquid chromatography, mass spectrometry, and enzymatic detection. In some embodiments, the variant barttin polypeptide is a variant of SEQ ID NO:2. In some embodiments, the variant barttin polypeptide is selected from the group consisting of SEQ ID NOs: 5, 10, and 12. In some embodiments, the variant barttin nucleic acid is a variant of SEQ ID NO:1. In some embodiments, the variant barttin nucleic acid is selected from the group consisting of SEQ ID NOs: 3, 4, 6, 7, 8, and 11. In some embodiments, the biological sample is selected from the group consisting of a blood sample, a tissue sample, a urine sample, and an amniotic fluid sample.

DESCRIPTION OF THE FIGURES

FIG. 2 shows haplotype analysis on chromosome 1p32.3.

FIG. 7 shows human cDNA (SEQ ID NO: 1) and deduced amino acid (SEQ ID NO:2) sequences of human and murine BSND. The last in-frame stop codon preceding the start codon, the start codon, stop codon, and polyadenylation site are shown in bold. Exons 2 and 4 are dotted underlined. Human deduced amino acid sequence is shown below cDNA sequence. Putative transmembrane helices are underlined. Divergences in mouse (SEQ ID NO:23) are given below human amino acid sequence with identities indicated by asterisks and codon positions absent from murine Bsnd as dashes. Numbering for deduced amino acid sequence is given on the left, for nucleotide sequence on the right beginning with the start codon. Mutations found in BS patients are highlighted by shaded boxes.

FIG. 9 shows Basic structural and functional features of barttin. a, Proposed topology. The PY motif (box) of Barttin (SEQ ID NO:31) is compared with similar motifs of ENaC (α-ENaC: SEQ ID NO:27; β-ENaC: SEQ ID NO:28; γ-ENaC: SEQ ID NO:29) and ClC-5 (SEQ ID NO:30) (ref. 14) (inset). The asterisk shows the tyrosine mutated to alanine in barttin (Y98A). Truncations are indicated by slashes and the number of the stop codon. b, Effect of truncated barttin on ClC-K1 in oocytes. c, Effect of the PY-motif mutation Y98A ('PY') on ClC-Ka (left) and ClC-Kb (right).

DEFINITIONS

Figure 1:
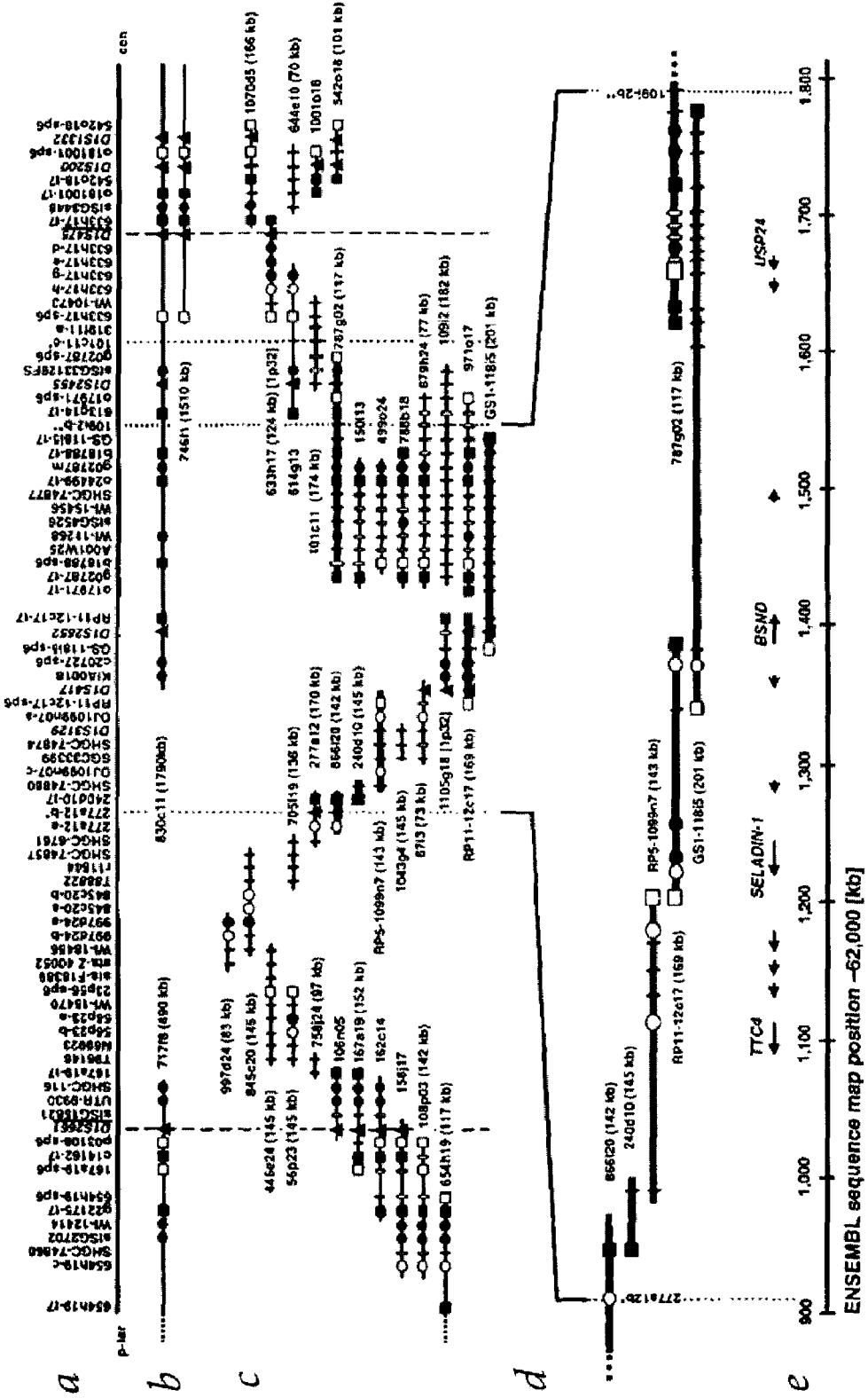
FIG. 1 shows the physical and genetic mapping of BSND on human chromosome 1p32.3. a, Markers mapped to the BSND region. p-ter, telomeric; cen, centromeric. b, A YAC contig and c, a BAC/PAC contig were constructed for the interval (thick vertical dashed lines) between markers D1S2661 and D1S475 (underlined). d, Enlarged view of the 900-kb critical interval between flanking markers 277a12-b and 109i2-b. e, Transcriptional map of the BSND locus. Putative genes as predicted by GENESCAN are shown as horizontal arrows in the direction of transcription. The symbols of known genes and BSND are indicated.

To facilitate understanding of the invention, a number of terms are defined below.

As used herein, the term "BSND" or "barttin" when used in reference to a protein or nucleic acid refers to a protein or nucleic acid encoding a protein that, in some mutant forms, is correlated with Bartter's syndrome. The term BSND encompasses both proteins that are identical to wild-type BSND and those that are derived from wild type BSND (e.g., variants of BSND or chimeric genes constructed with portions of BSND coding regions). In some embodiments, the "BSND" is the wild type nucleic acid (SEQ ID NO: 1) or amino acid (SEQ ID NO:2) sequence. In other embodiments, the "BSND" is a variant or mutant (e.g., including, but not limited to, the nucleic acid sequences described by SEQ ID NOS: 3, 4, 6, 7, 8, and 11 and the amino acid sequences described by SEQ ID NOS: 5, 10, and 12.

As used herein, the term "instructions for using said kit for said detecting the presence or absence of a variant barttin nucleic acid or polypeptide in said biological sample" includes instructions for using the reagents contained in the kit for the detection of variant and wild type barttin polypeptides. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4)Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., BSND). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "BSND gene" refers to the full-length BSND nucleotide sequence (e.g., contained in SEQ ID NO: 1). However, it is also intended that the term encompass fragments of the BSND sequence, mutants (e.g., SEQ ID NOS: 3, 4, 6, 7, 8, and 11) as well as other domains within the full-length BSND nucleotide sequence. Furthermore, the terms "BSND nucleotide sequence" or "BSND polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42 C when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length.

One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Liprnan [Pearson and Lipman, *Proc. Natl. Acad. Sci. (U.S.A.)* 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., BSND).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., the BSND gene).

As used herein, the term "detection assay" refers to an assay for detecting the presence of absence of variant nucleic acid sequences (e.g., polymorphism or mutations) in a given allele of a particular gene (e.g., the BSND gene). Examples of suitable detection assays include, but are not limited to, those described below in Section III B.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding BSND includes, by way of example, such nucleic acid in cells ordinarily expressing BSND where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, BSND antibodies are purified by removal of contaminating non-immunoglobulin proteins; they are also purified by the removal of immunoglobulin that does not bind BSND. The removal of non-immunoglobulin proteins and/or the removal of immunoglobulins that do not bind BSND results in an increase in the percent of BSND-reactive immunoglobulins in the sample. In another example, recombinant BSND polypeptides are expressed in bacterial host cells and the polypeptides are purified by the removal of host cell proteins; the percent of recombinant BSND polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning. A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced BSND transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding BSND (e.g., SEQ ID NO:1) or fragments thereof may be employed as hybridization probes. In this case, the BSND encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "entering" as in "entering said genetic variation information into said computer" refers to transferring information to a "computer readable medium." Information may be transferred by any suitable method, including but not limited to, manually (e.g., by typing into a computer) or automated (e.g., transferred from another "computer readable medium" via a "processor").

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

DETAILED DESCRIPTION OF THE INVENTION

The present invention relates to the BSND (barttin) protein and nucleic acids encoding the BSND protein. The present invention provides assays for the detection of BSND and barttin polymorphisms and mutations associated with disease states.

I. BSND Polynucleotides

As described above, a new gene associated with Barterr's syndrome has been discovered. Accordingly, the present invention provides nucleic acids encoding BSND genes, homologs, variants (e.g., polymorphisms and mutants), including but not limited to, those described in SEQ ID NO: 1. In some embodiments, the present invention provide polynucleotide sequences that are capable of hybridizing to SEQ ID NO: 1 under conditions of low to high stringency as long as the polynucleotide sequence capable of hybridizing encodes a protein that retains a biological activity of the naturally occurring BSND. In some embodiments, the protein that retains a biological activity of naturally occurring BSND is 70% homologous to wild-type BSND, preferably 80% homologous to wild-type BSND, more preferably 90% homologous to wild-type BSND, and most preferably 95% homologous to wild-type BSND. In preferred embodiments, hybridization conditions are based on the melting temperature ($T_m$) of the nucleic acid binding complex and confer a defined "stringency" as explained above (See e.g., Wahl, et al., Meth. Enzymol., 152:399-407 [1987], incorporated herein by reference).

In other embodiments of the present invention, additional alleles of BSND are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Examples of the alleles of the present invention include those encoded by SEQ ID NOs:1 (wild type) and disease alleles described herein (e.g., SEQ ID NOs: 3, 4, 6, 7, 8, and 11).

In still other embodiments of the present invention, the nucleotide sequences of the present invention may be engineered in order to alter an BSND coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of BSND may be extended utilizing the nucleotide sequence (e.g., SEQ ID NO: 1) in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 [1993]). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTER-FINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed BSND sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., BSND function) for such purposes as altering the biological activity (e.g., prevention of kidney disease or deafness). Such modified peptides are considered functional equivalents of peptides having an activity of BSND as defined herein. A modified peptide can be produced in which the nucleotide sequence encoding the polypeptide has been altered, such as by substitution, deletion, or addition. In particularly preferred embodiments, these modifications do not significantly reduce the biological activity of the modified BSND. In other words, construct "X" can be evaluated in order to determine whether it is a member of the genus of modified or variant BSND's of the present invention as defined functionally, rather than structurally. In preferred embodiments, the activity of variant BSND polypeptides is evaluated by methods described herein (e.g., the generation of transgenic animals).

Moreover, as described above, variant forms of BSND are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of BSND disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, W H Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a BSND coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

II. BSND Polypeptides

In other embodiments, the present invention provides BSND polynucleotide sequences that encode BSND polypeptide sequences (e.g., the polypeptide of SEQ ID NO:2). Other embodiments of the present invention provide fragments, fusion proteins or functional equivalents of these BSND proteins. In some embodiments, the present invention provides mutants of BSND (e.g., SEQ ID NOs: 5, 10, and 12). In still other embodiment of the present invention, nucleic acid sequences corresponding to BSND variants, homologs, and mutants may be used to generate recombinant DNA molecules that direct the expression of the BSND variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO:1 that encode substantially the same or a functionally equivalent amino acid sequence, may be used to clone and express BSND. In general, such polynucleotide sequences hybridize to SEQ ID NO:1 under conditions of high to medium stringency as described above. As will be understood by those of skill in the art, it may be advantageous to produce BSND-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of BSND expression or to produce recombinant RNA transcripts having desirable properties, such as a longer half-life, than transcripts produced from naturally occurring sequence.

1. Vectors for Production of BSND

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1, 3, 4, 6, 7, 8, and 11). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NO:1) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psix174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of BSND

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of BSND

The present invention also provides methods for recovering and purifying BSND from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NO: 1) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of BSND

In addition, the present invention provides fragments of BSND (i.e., truncation mutants). In some embodiments of the present invention, when expression of a portion of the BSND protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing BSND

The present invention also provides fusion proteins incorporating all or part of BSND. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a BSND protein. In some embodiments of the present invention, the VP6 capsid protein of rotavirus is used as an immunologic carrier protein for portions of the BSND polypeptide, either in the monomeric form or in the form of a viral particle. In other embodiments of the present invention, the nucleic acid sequences corresponding to the portion of BSND against which antibodies are to be raised can be incorporated into a fusion gene construct which includes coding sequences for a late vaccinia virus structural protein to produce a set of recombinant viruses expressing fusion proteins comprising a portion of BSND as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of BSND and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of BSND is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the BSND proteins can also be expressed and presented by bacterial cells.

In addition to utilizing fusion proteins to enhance immunogenicity, it is widely appreciated that fusion proteins can also facilitate the expression of proteins, such as the BSND protein of the present invention. Accordingly, in some embodiments of the present invention, BSND can be generated as a glutathione-S-transferase (i.e., GST fusion protein). It is contemplated that such GST fusion proteins will enable easy purification of BSND, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of BSND, can allow purification of the expressed BSND fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of BSND

Still other embodiments of the present invention provide mutant or variant forms of BSND (i.e., muteins). It is possible to modify the structure of a peptide having an activity of BSND for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject BSND proteins as defined herein. A modified peptide can be produced in which the amino acid sequence has been altered, such as by amino acid substitution, deletion, or addition.

Moreover, as described above, variant forms (e.g., mutants or polymorphic sequences) of the subject BSND proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present BSND proteins, as well as truncation mutants, and is especially useful for identifying potential variant sequences (i.e., mutants or polymorphic sequences) that are involved in kidney disease or resistance to kidney disease. The purpose of screening such combinatorial libraries is to generate, for example, novel BSND variants that can act as either agonists or antagonists, or alternatively, possess novel activities all together.

Therefore, in some embodiments of the present invention, BSND variants are engineered by the present method to provide altered (e.g., increased or decreased) biological activity. In other embodiments of the present invention, combinatorially-derived variants are generated which have a selective potency relative to a naturally occurring BSND. Such proteins, when expressed from recombinant DNA constructs, can be used in gene therapy protocols.

Still other embodiments of the present invention provide BSND variants that have intracellular half-lives dramatically different than the corresponding wild-type protein. For example, the altered protein can be rendered either more stable or less stable to proteolytic degradation or other cellular process that result in destruction of, or otherwise inactivate BSND. Such variants, and the genes which encode them, can be utilized to alter the location of BSND expression by modulating the half-life of the protein. For instance, a short half-life can give rise to more transient BSND biological effects and, when part of an inducible expression system, can allow tighter control of BSND levels within the cell. As above, such proteins, and particularly their recombinant nucleic acid constructs, can be used in gene therapy protocols.

In still other embodiments of the present invention, BSND variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of BSND homologs, variants or other related proteins are aligned, preferably to promote the highest homology possible. Such a population of variants can include, for example, BSND homologs from one or more species, or BSND variants from the same species but which differ due to mutation or polymorphisms. Amino acids that appear at each position of the aligned sequences are selected to create a degenerate set of combinatorial sequences.

In a preferred embodiment of the present invention, the combinatorial BSND library is produced by way of a degenerate library of genes encoding a library of polypeptides which each include at least a portion of potential BSND protein sequences. For example, a mixture of synthetic oligonucleotides can be enzymatically ligated into gene sequences such that the degenerate set of potential BSND sequences are expressible as individual polypeptides, or alternatively, as a set of larger fusion proteins (e.g., for phage display) containing the set of BSND sequences therein.

There are many ways by which the library of potential BSND homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential BSND sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87:6378 [1990]; each of which is herein incorporated by reference; as well as U.S. Pat. Nos. 5,223,409, 5,198,346, and 5,096,815; each of which is incorporated herein by reference).

It is contemplated that the BSND nucleic acids (e.g., SEQ ID NO:1, and fragments and variants thereof) can be utilized as starting nucleic acids for directed evolution. These techniques can be utilized to develop BSND variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for BSND activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for BSND activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of BSND homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of BSND

In an alternate embodiment of the invention, the coding sequence of BSND is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire BSND amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of BSND, or any part thereof, may be altered during direct synthesis and/or combined using chemical methods with other sequences to produce a variant polypeptide.

III. Detection of BSND Alleles

In some embodiments, the present invention provides methods of detecting the presence of wild or variant (e.g., mutant or polymorphic) BSND nucleic acids or polypeptides. The detection of mutant BSND polypeptides finds use in the diagnosis of disease (e.g., Bartter's syndrome).

A. BSND Alleles

In some embodiments, the present invention includes alleles of BSND that increase a patient's susceptibility to Bartter's syndrome (e.g., including, but not limited to, SEQ ID NOs: 3, 4, 6, 7, 8, and 11). However, the present invention is not limited to the mutation described in SEQ ID NOs: 3, 4, 6, 7, 8, and 11. Any mutation that results in the undesired phenotype (e.g., Bartter's syndrome with deafness and kidney failure) is within the scope of the present invention. Exemplary alleles are described in Table 2 and FIG. 7.

TABLE 2

BSND Alleles

| Nucleotide change | SEQ ID NO: (Nucleic Acid) | SEQ ID NO (Amino Acid) |
|---|---|---|
| Wild Type | 1 | 2 |
| A1T | 3 | |
| C22T (R8W) | 4 | 5 |
| 157_IVSI + 20del41 | 6 | |
| EX3_EX4del | 7 | |
| G3A | 8 | |
| G28A (G10S) | 9 | 10 |
| G23T (R8L) | 11 | 12 |

B. Detection of BSND Alleles

Accordingly, the present invention provides methods for determining whether a patient has an increased susceptibility to Bartter's syndrome (e.g., Bartter's sydrome eith sensorineural deafness and kidney failure by determining whether the individual has a variant BSND allele. In other embodiments, the present invention provides methods for providing a prognosis of increased risk for kidney failure or deafness to an individual based on the presence or absence of one or more variant alleles of BSND.

A number of methods are available for analysis of variant (e.g., mutant or polymorphic) nucleic acid sequences. Assays for detection variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele of BSND (e.g., to the region of polymorphism or mutation). Both sets of primers are used to amplify a sample of DNA. If only the mutant primers result in a PCR product, then the patient has the mutant BSND allele. If only the wild-type primers result in a PCR product, then the patient has the wild type allele of BSND.

3. Mutational Detection by dHPLC

In some embodiments of the present invention, variant sequences are detected using a PCR-based assay with consecutive detection of nucleotide variants by dHPLC (denaturing high performance liquid chromatography). Exemplary systems and Methods for dHPLC include, but are not limited to, WAVE (Transgenomic, Inc; Omaha, Nebr.) or VARIAN equipment (Palo Alto, Calif.).

4. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assay

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888, 780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

5. Hybridization Assays

In preferred embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or non-specifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by inkjet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/ mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLI-TAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

6. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605, 798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

7. Detection of Variant BSND Proteins

In other embodiments, variant (e.g., truncated) BSND polypeptides are detected (e.g., including, but not limited to, those described in SEQ ID NOs: 5, 10, and 12. Any suitable method may be used to detect truncated or mutant BSND polypeptides including, but not limited to, those described below.

a) Cell Free Translation

For example, in some embodiments, cell-free translation methods from Ambergen, Inc. (Boston, Mass.) are utilized. Ambergen, Inc. has developed a method for the labeling, detection, quantitation, analysis and isolation of nascent proteins produced in a cell-free or cellular translation system without the use of radioactive amino acids or other radioactive labels. Markers are aminoacylated to tRNA molecules. Potential markers include native amino acids, non-native amino acids, amino acid analogs or derivatives, or chemical moieties. These markers are introduced into nascent proteins from the resulting misaminoacylated tRNAs during the translation process.

One application of Ambergen's protein labeling technology is the gel free truncation test (GFTT) assay (See e.g., U.S. Pat. No. 6,303,337, herein incorporated by reference). In some embodiments, this assay is used to screen for truncation mutations in a barttin protein. In the GFTT assay, a marker (e.g., a fluorophore) is introduced to the nascent protein during translation near the N-terminus of the protein. A second and different marker (e.g., a fluorophore with a different emission wavelength) is introduced to the nascent protein near the C-terminus of the protein. The protein is then separated from the translation system and the signal from the markers is measured. A comparison of the measurements from the N and C terminal signals provides information on the fraction of the molecules with C-terminal truncation (i.e., if the normalized signal from the C-terminal marker is 50% of the signal from the N-terminal marker, 50% of the molecules have a C-terminal truncation).

b) Antibody Binding

In still further embodiments of the present invention, antibodies (See below for antibody production) are used to determine if an individual contains an allele encoding a variant BSND gene. In preferred embodiments, antibodies are utilized that discriminate between variant (i.e., truncated proteins); and wild-type proteins (SEQ ID NOs:2). In some embodiments, the antibodies are directed to the C-terminus of BSND. Proteins that are recognized by the N-terminal, but not the C-terminal antibody are truncated. In some embodiments, quantitative immunoassays are used to determine the ratios of C-terminal to N-terminal antibody binding. In other embodiments, antibodies that differentially bind to wild type or variant forms of BSND are utilized.

Antibody binding is detected by techniques known in the art (e.g., radioiimunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the result of the immunoassay is utilized.

In other embodiments, the immunoassay described in U.S. Pat. Nos. 5,599,677 and 5,672,480; each of which is herein incorporated by reference.

8. Kits for Analyzing Risk of Bartter's Syndrome

The present invention also provides kits for determining whether an individual contains a wild-type or variant (e.g., mutant or polymorphic) allele or polypeptide of BSND. In some embodiments, the kits are useful determining whether the subject is at risk of developing Bartter's syndrome with deafness and kidney failure. The diagnostic kits are produced in a variety of ways. In some embodiments, the kits contain at least one reagent for specifically detecting a mutant BSND allele or protein. In preferred embodiments, the reagent is a nucleic acid that hybridizes to nucleic acids containing the mutation and that does not bind to nucleic acids that do not contain the mutation. In other preferred embodiments, the reagents are primers for amplifying the region of DNA containing the mutation. In still other embodiments, the reagents are antibodies that preferentially bind either the wild-type or truncated BSND proteins.

In some embodiments, the kit contains instructions for determining whether the subject is at risk for developing Bartter's syndrome with sensorineural deafness and kidney failure. In preferred embodiments, the instructions specify that risk for developing Bartter's syndrome with sensorineural deafness and kidney failure is determined by detecting the presence or absence of a mutant BSND allele in the subject, wherein subjects having an mutant (e.g., truncated) allele are at greater risk for Bartter's syndrome with sensorineural deafness and kidney failure.

The presence of absence of a disease-associated mutation in a BSND gene can be used to may therapeutic or other medical decisions. For example, couples with a family history of Bartter's syndrome with sensorineural deafness and kidney failure may choose to conceive a child via in vitro fertilization and pre-implantation genetic screening. In this case, fertilized embryos are screened for mutant (e.g., disease associated) alleles of the BSND gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a BSND allele known to be associated with Bartter's syndrome with sensorineural deafness and kidney failure allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packages in any suitable manner, typically with the elements in a single container or various containers as necessary along with a sheet of instructions for carrying out the test. In some embodiments, the kits also preferably include a positive control sample.

9. Bioinformatics

In some embodiments, the present invention provides methods of determining an individual's risk of developing Bartter's syndrome with sensorineural deafness and kidney failure based on the presence of one or more variant alleles of BSND. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting Bartter's syndrome with sensorineural deafness and kidney failure associated with a given polymorphism, as well as the sequences). In some embodiments, one of the computers stores application programs (e.g., for analyzing the results of detection assays). Results are then delivered to the user (e.g., via one of the computers or via the internet.

For example, in some embodiments, a computer-based analysis program is used to translate the raw data generated by the detection assay (e.g., the presence, absence, or amount of a given BSND allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant BSND genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing Bartter's syndrome with sensorineural deafness and kidney failure) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

IV. Generation of BSND Antibodies

The present invention provides isolated antibodies or antibody fragments (e.g., FAB fragments). Antibodies can be generated to allow for the detection of BSND protein. The antibodies may be prepared using various immunogens. In one embodiment, the immunogen is a human BSND peptide to generate antibodies that recognize human BSND. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against BSND. For the production of antibody, various host animals can be immunized by injection with the peptide corresponding to the BSND epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward BSND, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing BSND specific single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for BSND.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay N.Y., Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of BSND (e.g., for Western blotting), measuring levels thereof in appropriate biological samples, etc. The antibodies can be used to detect BSND in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human BSND using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of BSND detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of BSND or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of BSND. Such antibodies can also be used diagnostically to measure abnormal expression of BSND, or the aberrant formation of protein complexes, which may be indicative of a disease state.

V. Gene Therapy Using BSND

The present invention also provides methods and compositions suitable for gene therapy to alter BSND expression, production, or function. As described above, the present invention provides human BSND genes and provides methods of obtaining BSND genes from other species. Thus, the methods described below are generally applicable across many species. In some embodiments, it is contemplated that the gene therapy is performed by providing a subject with a wild-type allele of BSND (i.e., an allele that does not contain a BSND disease (e.g., free of disease causing polymorphisms or mutations). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VI. Transgenic Animals Expressing Exogenous BSND Genes and Homologs, Mutants, and Variants Thereof The present invention contemplates the generation of transgenic animals comprising an exogenous BSND gene or homologs, mutants, or variants thereof. In preferred embodiments, the transgenic animal displays an altered phenotype as compared to wild-type animals. In some embodiments, the altered phenotype is the overexpression of mRNA for a BSND gene as compared to wild-type levels of BSND expression. In other embodiments, the altered phenotype is the decreased expression of mRNA for an endogenous BSND gene as compared to wild-type levels of endogenous BSND expression. In some preferred embodiments, the transgenic animals comprise mutant (e.g., truncated) alleles of BSND. Methods for analyzing the presence or absence of such phenotypes include Northern blotting, mRNA protection assays, and RT-PCR. In other embodiments, the transgenic mice have a knock out mutation of the BSND gene. In preferred embodiments, the transgenic animals display a Bartter's syndrome with sensorineural deafness and kidney failure phenotype.

Such animals find use in research applications (e.g., identifying signaling pathways that BSND is involved in), as well as drug screening applications (e.g., to screen for drugs that prevent or treat Bartter's syndrome with sensorineural deafness and kidney failure. For example, in some embodiments, test compounds (e.g., a drug that is suspected of being useful to treat Bartter's syndrome with sensorineural deafness and kidney failure) and control compounds (e.g., a placebo) are administered to the transgenic animals and the control animals and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci.

USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which the LRRs of BSND are deleted). Methods for homologous recombination are described in U.S. Pat. No. 5,614,396, incorporated herein by reference.

VIII. Drug Screening Using BSND

As describe below, experiments conducted during the course of development of the present invention demonstrated that the protein barttin associates with ClC-Ka or ClC-Kb to functional heteromeric Cl channels in epithelia of the kidney and the inner ear. Mutations in barttin that were found in BSND (Bartter syndrome with sensorineural deafness) abolish, or greatly reduce, the function of this channel. ClC-Kibarttin heteromeric channels are crucial for transepithelial transport of salt and fluid in specific nephron segments and in epithelia of the cochlea and the vestibular organ.

Accordingly, it is contemplated that heteromers of ClC-Ka/barttin and ClC-Kb/barttin (or the respective non-human homologs) find use as targets to develop drugs that interact with these heteromeric proteins. These drugs are used to inhibit, enhance, or otherwise modulate the function of the heteromeric channel.

In some embodiments, inhibitors of ClC-K/barttin channels are useful as diuretics. As such, they may not only be used to increase urinary output, but also for treating various kidney diseases including acute renal failure, and can be used in the treatment of hypertension. The present invention is not limited to a particular mechanism. Indeed, an understanding of the mechanism is not necessary to practice the present invention. Nonetheless, it is contemplated that the fact that ClC-K/barttin channels are present in basolateral membranes implies that drugs acting on ClC-Kibarttin access their targets from the blood side. This is in contrast to currently used diuretics such as furosemide, thiazides, amiloride and their derivatives, which act on luminal transport proteins. Thus, substances targeting ClC-KIbarttin channels are contemplated to be effective also in conditions such as renal failure, in which a drop in glomerular filtration prevents the above-mentioned conventional diuretics to reach their target proteins.

In other embodiments, activators or other modulators of ClC-K/barttin are used in treating other renal diseases (e.g., to inhibit renal salt and fluid loss or treat low blood pressure).

In yet other embodiments, substances altering the function of ClC-K/barttin channels (inhibitors, activators, modulators) are used to treat diseases of the inner ear, including (but not limited to) hearing loss, tinnitus, vertigo, and Meniere's disease.

The present invention is not limited to a particular mechanism. Indeed, an understanding of the mechanism is not necessary to practice the present invention. Nonetheless, it is contemplated that, based on the discovery that ClC-K/barttin channels are regulated by a motif (PY-motif) on barttin, that compounds that regulate ClC-K/barttin function additionally find use in treating kidney disease and deafness. Thus, in some embodiments, substances are identified that activate, inhibit, or otherwise modulate the function of ClC-K/barttin by targeting this mechanism of regulation.

Experiments conducted during the course of development of the present invention comprising the identification and functional testing of a. 'PY-motif' on barttin shows that some mutations in barttin can lead to an increased activity of this channel that entails hypertension (high blood pressure). The present invention is not limited to a particular mechanism. Indeed, an understanding of the mechanism is not necessary to practice the present invention. Nonetheless, it is contemplated that barttin causes, or contributes to, high blood pressure. Thus, in other embodiments, the present invention provides methods of screening for compounds that are useful in the treatment of high blood pressure.

A. Drug Screening

Accordingly, in some embodiments, the isolated nucleic acid and polypeptides of BSND (e.g., SEQ ID NOS: 1-12) and related proteins and nucleic acids are used in drug screening applications for compounds that alter (e.g., enhance or inhibit) barttin activity and signaling.

In one screening method, the two-hybrid system is used to screen for compounds (e.g., drug) capable of altering (e.g., inhibiting) BSND function(s) (e.g., interaction with a binding partner) in vitro or in vivo. In one embodiment, a GAL4 binding site, linked to a reporter gene such as lacZ, is contacted in the presence and absence of a candidate compound with a GAL4 binding domain linked to a BSND fragment and a GAL4 transactivation domain II linked to a binding partner fragment. Expression of the reporter gene is monitored and a decrease in the expression is an indication that the candidate compound inhibits the interaction of BSND with the binding partner. Alternately, the effect of candidate compounds on the interaction of BSND with other proteins (e.g., proteins known to interact directly or indirectly with the binding partner) can be tested in a similar manner.

In another screening method, candidate compounds are evaluated for their ability to alter BSND signaling by contacting BSND, binding partners, binding partner-associated proteins, or fragments thereof, with the candidate compound and determining binding of the candidate compound to the peptide. The protein or protein fragments is/are immobilized using methods known in the art such as binding a GST-BSND fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., *E. coli* XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate BSND physiological effects (e.g., kidney disease).

In another screening method, one of the components of the BSND/binding partner signaling system, is immobilized. Polypeptides can be immobilized using methods known in the art, such as adsorption onto a plastic microtiter plate or specific binding of a GST-fusion protein to a polymeric bead containing glutathione. For example, GST-BSND is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of BSND with the other peptide. A variation of this method allows for the screening of compounds that are capable of disrupting a previously-formed protein/protein complex. For example, in some embodiments a complex comprising BSND or a BSND fragment bound to another peptide is immobilized as described above and contacted with a candidate compound. The dissolution of the complex by the candidate compound correlates with the ability of the compound to disrupt or inhibit the interaction between BSND and the other peptide.

Another technique for drug screening provides high throughput screening for compounds having suitable binding affinity to BSND peptides and is described in detail in WO 84/03564, incorporated herein by reference. Briefly, large numbers of different small peptide test compounds are synthesized on a solid substrate, such as plastic pins or some other surface. The peptide test compounds are then reacted with BSND peptides and washed. Bound BSND peptides are then detected by methods well known in the art.

Another technique uses BSND antibodies, generated as discussed above. Such antibodies capable of specifically binding to BSND peptides compete with a test compound for binding to BSND. In this manner, the antibodies can be used to detect the presence of any peptide that shares one or more antigenic determinants of the BSND peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with BSND and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding BSND or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by BSND in operable association with a reporter gene (See Inohara et al., J. Biol. Chem. 275:27823 [2000] for a description of the luciferase reporter construct pBVIx-Luc). Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, calorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to BSND of the present invention, have an inhibitory (or stimulatory) effect on, for example, BSND expression or BSND activity, or have a stimulatory or inhibitory effect on, for example, the expression or activity of a BSND substrate. Compounds thus identified can be used to modulate the activity of target gene products (e.g., BSND genes) either directly or indirectly in a therapeutic protocol, to elaborate the biological function of the target gene product, or to identify compounds that disrupt normal target gene interactions. Compounds which stimulate the activity of a variant BSND or mimic the activity of a non-functional variant are particularly useful in the treatment of kidney disease, high blood pressure, and deafness.

In one embodiment, the invention provides assays for screening candidate or test compounds that are substrates of a BSND protein or polypeptide or a biologically active portion thereof. In another embodiment, the invention provides assays for screening candidate or test compounds that bind to or modulate the activity of a BSND protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a BSND protein or biologically active portion thereof is contacted with a test compound, and the ability of the test compound to the modulate BSND's activity is determined. Determining the ability of the test compound to modulate BSND activity can be accomplished by monitoring, for example, changes in enzymatic activity. The cell, for example, can be of mammalian origin.

The ability of the test compound to modulate BSND binding to a compound, e.g., a BSND substrate, can also be evaluated. This can be accomplished, for example, by coupling the compound, e.g., the substrate, with a radioisotope or enzymatic label such that binding of the compound, e.g., the substrate, to a BSND can be determined by detecting the labeled compound, e.g., substrate, in a complex.

Alternatively, the BSND is coupled with a radioisotope or enzymatic label to monitor the ability of a test compound to modulate BSND binding to a BSND substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a BSND substrate) to interact with a BSND with or without the labeling of any of the interactants can be evaluated. For example, a microphysiometer can be used to detect the interaction of a compound with a BSND without the labeling of either the compound or the BSND (McConnell et al. Science 257: 1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and BSND.

In yet another embodiment, a cell-free assay is provided in which a BSND protein or biologically active portion thereof is contacted with a test compound and the ability of the test compound to bind to the BSND protein or biologically active portion thereof is evaluated. Preferred biologically active portions of the BSND proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 15 the assay should be maximal. An FRET binding event can be conveniently measured through standard fluorometric detection means well known in the art (e.g., using a fluorimeter).

In another embodiment, determining the ability of the BSND protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance.(SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize BSND, an anti-BSND antibody or its target molecule to facilitate separation of complexed from non-complexed forms of one or both of the proteins, as well as to accommodate automation of the assay. Binding of a test compound to a BSND protein, or interaction of a BSND protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-BSND fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or BSND protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of BSND binding or activity determined using standard techniques. Other techniques for immobilizing either BSND protein or a target molecule on matrices include using conjugation of biotin and streptavidin. Biotinylated BSND protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with BSND protein or target molecules but which do not interfere with binding of the BSND protein to its target molecule. Such antibodies can be derivatized to the wells of the plate, and unbound target or BSND protein trapped in the wells by antibody conjugation. Methods for detecting such complexes, in addition to those described above for the GST-immobilized complexes, include immunodetection of complexes using antibodies reactive with the BSND protein or target molecule, as well as enzyme-linked assays which rely on detecting an enzymatic activity associated with the BSND protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the BSND protein or biologically active portion thereof with a known compound that binds the BSND to form an assay mixture, contacting the assay mixture with a test compound, and determining the ability of the test compound to interact with a BSND protein, wherein determining the ability of the test compound to interact with a BSND protein includes determining the ability of the test compound to preferentially bind to BSND or biologically active portion thereof, or to modulate the activity of a target molecule, as compared to the known compound.

To the extent that BSND can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, BSND protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent W0 94/10300; each of which is herein incorporated by reference), to identify other proteins, that bind to or interact with BSND ("BSND-binding proteins" or "BSND-bp") and are involved in BSND activity. Such BSND-bps can be activators or inhibitors of signals by the BSND proteins or targets as, for example, downstream elements of a BSND-mediated signaling pathway.

Modulators of BSND expression can also be identified. For example, a cell or cell free mixture is contacted with a candidate compound and the expression of BSND mRNA or protein evaluated relative to the level of expression of BSND mRNA or protein in the absence of the candidate compound. When expression of BSND MRNA or protein is greater in the presence of the candidate compound than in its absence, the candidate compound is identified as a stimulator of BSND mRNA or protein expression. Alternatively, when expression of BSND mRNA or protein is less (i.e., statistically significantly less) in the presence of the candidate compound than in its absence, the candidate compound is identified as an inhibitor of BSND mRNA or protein expression. The level of BSND mRNA or protein expression can be determined by methods described herein for detecting BSND mRNA or protein.

A modulating agent can be identified using a cell-based or a cell free assay, and the ability of the agent to modulate the activity of a BSND protein can be confirmed in vivo, e.g., in an animal such as an animal model for a disease (e.g., an animal with kidney disease; See e.g., Hildenbrandt and Otto, J. Am. Soc. Nephrol. 11:1753 [2000]).

B. Therapeutic Agents

This invention further pertains to novel agents identified by the above-described screening assays. Accordingly, it is within the scope of this invention to further use an agent identified as described herein (e.g., a BSND modulating agent or mimetic, a BSND specific antibody, or a BSND-binding partner) in an appropriate animal model (such as those described herein) to determine the efficacy, toxicity, side effects, or mechanism of action, of treatment with such an agent. Furthermore, as described above, novel agents identified by the above-described screening assays can be, e.g., used for treatments of kidney disease (e.g., including, but not limited to, Bartter's sydrome), deafness, and high blood pressure.

IX. Pharmaceutical Compositions Containing BSND Nucleic Acid, Peptides, and Analogs The present invention further provides pharmaceutical compositions which may comprise all or portions of BSND polynucleotide sequences, BSND polypeptides, inhibitors or antagonists of BSND bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant BSND alleles (e.g., Bartter's syndrome with deafness and kidney failure). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, BSND nucleotide and BSND amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, BSND polynucleotide sequences or BSND amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of BSND may be that amount that suppresses apoptosis. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of BSND, conditions indicated on the label may include treatment of condition related to apoptosis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts BSND levels.

A therapeutically effective dose refers to that amount of BSND that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for BSND than for the inhibitors of BSND. Administration to the bone marrow may necessitate delivery in a manner different from intravenous injections.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin); Fisher (Fisher Scientific, Pittsburgh, Pa.); Sigma (Sigma Chemical Co., St. Louis, Mo.); Promega (Promega Corp., Madison, Wis.); Perkin-Elmer (Perkin-Elmer/Applied Biosystems, Foster City, Calif.); Boehringer Mannheim (Boehringer Mannheim, Corp., Indianapolis, Ind.); Clonetech (Clonetech, Palo Alto, Calif.); Qiagen (Qiagen, Santa Clarita, Calif.); Stratagene (Stratagene Inc., La Jolla, Calif.); National Biosciences (National Biosciences Inc, Plymouth Minn.) and NEB (New England Biolabs, Beverly, Mass.), wt (wild-type); Ab (antibody); ESRD (end stage renal disease).

EXAMPLE 1

Mutation of BSND Causes Bartter Syndrome with Sensorineural Deafness and Kidney Failure A. Methods Patients.

Blood samples and pedigrees were obtained after informed consent from patients with BSND and their parents. Families F314, F591, F730, F786 and F791 were from Turkey, families F813 and F197 from northern Africa, F708 from Lebanon, F662 from the UK, F206 from France, and F542 was a Bedouin family from Israel. In all families except F662 the parents of the affected offspring were first-degree cousins. All patients fulfilled the diagnostic criteria of aBS and SND as described previously (Vollmer et al., Nephrol. Dial. Transplant, 15:970-974 (1998)). Detailed clinical data from the following patients has been published previously: F314 (V), F730 (VI), F786 (II), F791 (III) and F708 (IV) (Jeck et al., Pediatrics, 108:E5 (2001)).

Genomic Clones and STS Markers.

STS content mapping was carried out as described previously (Nothwang et al., Genomics, 47:276-285 (1998)). PAC clones were obtained from the RZPD. BAC clone GS1-118i5 were obtained from GenomeSystems. BAC GS 1-118i5 was submitted to the Sanger sequencing center and sequenced in its entirety. The genomic sequence of human BSND was submitted to GenBank. BAC/PAC preparation and PAC-end sequencing was carried out as previously described (Jeck et al., Pediatrics, 108:E5 (2001)). Primer sequences for newly generated STS markers are generally available.

Mutational Analysis and cDNA Clones.

Exon-flanking primers used for mutational analysis by direct sequencing were: sp5ex1f,

```
                                      (SEQ ID NO:13)
5'-GAGCAGAGAGAAGACCGAGTC-3';          sp5ex1r, (SEQ ID NO:14)
5'-TGTCTTCTCTCCCTGTGTAAGC-3';         sp5ex2f, (SEQ ID NO:15)
5'-TGCCTAACTCACAGAATTGAGAG-3';        sp5ex2r, (SEQ ID NO:16)
5'-ACAGAGGCTGTCTCTCCTTTG-3';          sp5ex3f, (SEQ ID NO:17)
5'-CTCTCCTTTTTAACCCTTGAACTG-3';       sp5ex3r, (SEQ ID NO:18)
5'-GACCACATACCCAAAGCAAAC-3';          sp5ex4f, (SEQ ID NO:19)
5'-CCATTTTGCAGATAGGGAAAC-3';          sp5ex4r, (SEQ ID NO:20)
5'-CGGGAAGGTGGATTATCCTAC-3'.
```

PCR primers flanking the 3,096-bp deletion found in family F708 were:

```
                                      (SEQ ID NO:21)
del708f, 5'-ATGGCACAGCCAAGAATGCTCCAG-3',
and (SEQ ID NO:22)
del708r, 5'-ATCTGGGCACAGGCGATCTCAAGGT-3'
```

Northern Blot Analysis.

A multiple-tissue northern blot with human adult poly (A)+RNA (Clontech) was hybridized with the respective cDNA probes. Hybridization conditions were 68° C. using ExpressHyb solution (Clontech). The final washing condition was in 0.1×SSC, 0.1% SDS at 50° C. for 40 min.

Fluorescent in situ Hybridization (FISH).

FISH analysis was carried out as previously described (Jeck et al., Pediatrics, 108:E5 (2001)).

Section in situ Hybridization Analysis.

From murine EST AI117061, a fragment by PCR was generated for the CDNA sequence encoding the amino acids from position 2 up to the stop codon and subcloned into pCR4-TOPO (Invitrogen) to construct subclone pCR4.Bart4. Next, a digoxigenin-labeled antisense riboprobe was generated from the 0.9-kb mouse Bsnd CDNA after linearization with SpeI and transcription with T7 RNA polymerase. Kidneys from 6-week-old mice and inner ears from 18.5-dpc embryos were fixed overnight in 4% paraformaldehyde, washed in PBS, dehydrated through a series of isopropanol dilutions, embedded in paraffin and sectioned at 10 m. In situ hybridization was carried out on these sections in accordance with a previously described method, (Lescher et al., Dev. Dyn. 213:440-451 (1998)), with the following modification: prehybridization with 800 microliter and hybridization with 200 microliter hybridization solution containing the antisense riboprobe, respectively, were carried out at 68° C. After the hybridization, all steps followed the procedure described for whole-mount in situ hybridization (Lescher et al., Dev. Dyn. 213:440-451 (1998)). Sections were mounted in Moviol and photographed using a Leica DC200 digital camera on a Leica M420 photomicroscope or under Nomarski optics using a Fujix digital camera HC300Z on a Zeiss Axioplan. Files were processed in Adobe Photoshop v.5.0 on a G4 PowerMacintosh.

Sequence Analysis and Protein Modeling.

Sequences were compared using the BLASTP/N/X programs (available at the Internet web site of ncbi at the nih) and used the program ATGpr in predicting the translation initiation site. For secondary-structure prediction, the program SMART (available from the Internet web site of embl) was used with TMpred at the Expasy site, which produced FIG. 3. Standard parameters were applied.

Accession Numbers.

The sequences of the full-length human BSND cDNA (accession number AY034632) and the full-length murine Bsnd cDNA (accession number AF391088) were submitted to GenBank. GenBank accession number for the human BAC clone GS1-115i5 containing the genomic BSND sequence is AL589790. Accession numbers for ESTs from the databases were: AI823652, AI301509, AI916510 and AI823955 for human, AI780751 and AI117061 for mouse, and AV601916 for the bovine sequence.

B. Results

To clone the BSND locus, a combined YAC/BAC/PAC contig was generated by sequence-tagged site (STS) content mapping in the 4-centimorgan (cM) interval between flanking markers D1S2661 and D1S475 as shown in FIG. 1a-c, and defined previously (Vollmer et al., Nephrol. Dial. Transplant 15:970-974 (1998)). Homozygosity mapping, (Lander et al., Science 236:1567-1570 (1987)), was used to refine the critical genetic region in ten families with BSND, each of which were consanguineous with the exception of family F662 (FIG. 2). Heterozygosity with respect to markers 277a12-b and 101c11-e restricted the critical region to less than 1 Mb (FIGS. 1a-c and FIG. 2). Extensive haplotype sharing was detected between five families of Turkish descent (FIG. 2). Under the hypothesis of haplotype sharing by descent, the critical genetic interval was narrowed further to <900 kb, as lack of sharing 109i2-b as a new centromeric flanking marker (FIGS. 1a-c and FIG. 2). Within this interval, a cloning gap persisted after extensive screening of human genomic PAC libraries (Ioannou et al., Nature Genetics 6:84-89 (1994)). The gap was also present within recent data from the human genome sequencing projects (The International Human Genome Mapping Consortium, Nature 409:934-941 (2001); Venter et al., Science 291:1304-1351 (2001)). By screening the human genomic BAC library BAC-5331 (GenomeSystems) using a modification of marker D1S2652, a single clone (GS1-118i5) was obtained, which was shown by STS content mapping to bridge the gap (FIGS. 1c,d). This clone was submitted to the Sanger Centre for sequencing.

Figure 6:
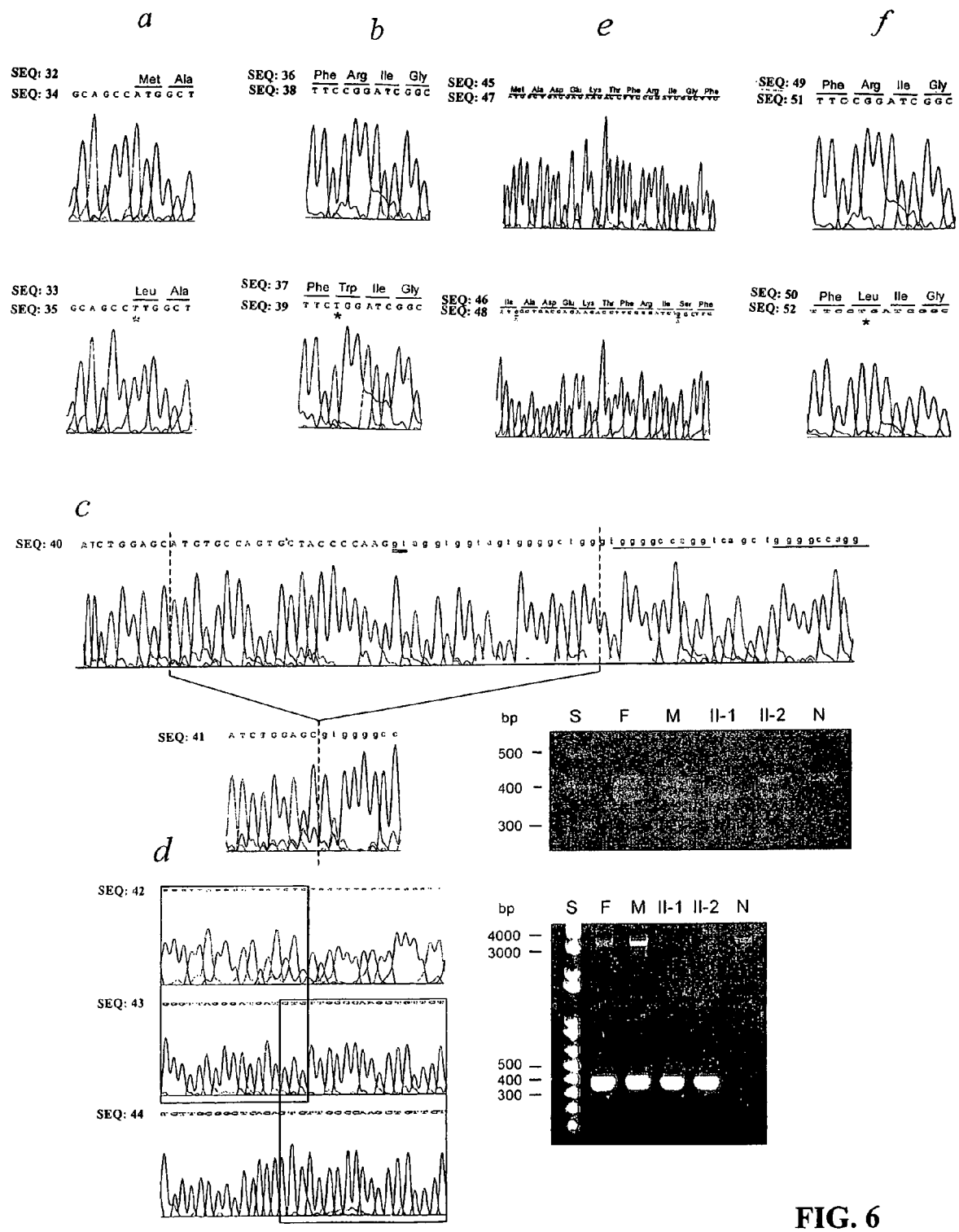
FIG. 6 shows mutations in BSND in 10 BSND kindred. In a-f the lower trace shows a sequence alteration in an affected individual, and the upper trace the respective wildtype sequence from an unrelated unaffected individual. Translation products are shown. Asterisks indicate position of base pair alterations. a, The 1A.T transversion within the START codon (substitution of methionine codon for leucine codon) will interfere with translation initiation. The mutation is shown for the affected individual of family F314. The upper panel shows SEQ ID NO: 32 (amino acid) and SEQ ID NO: 34 (nucleic acid) sequences. The upper panel shows SEQ ID NO: 33 (amino acid) and SEQ ID NO: 35 (nucleic acid) sequences. b, The 22C.T transition results in substitution of arginine for tryptophane in codon 8 in the affected individual of family F813. The upper panel shows SEQ ID NO: 36 (amino acid) and SEQ ID NO: 38 (nucleic acid) sequences. The lower panel shows SEQ ID NO: 37 (amino acid) and SEQ ID NO: 39 (nucleic acid) sequences c, In the affected child of family F197 (lower trace); SEQ ID NO: 41) a 41 base pair deletion (157_IVS1+20del41) abolishes 21 base pairs of exon 1 and 20 base pairs of intron 1 in comparison to wild type sequence (upper trace(SEQ ID NO: 40). Exon sequence is shown as upper case, intron sequence as lower case. The splice donor site is double underlined. A 10 bp direct repeat is underlined. The insert shows agarose gel electrophoresis of genomic PCR products of primers sp5ex1f and sp5ex1r for the wild type allele (415 bp) and/or the allele (374 bp) containing the 41 bp deletion for the father (F), the mother (M), the affected child (II-1), the unaffected child (II-2) of family F197 and a normal control individual (N). Size markers (S) are shown on the left. d, For the 3096 bp deletion of family F708 wild type sequence around the proximal breakpoint 885 bp upstream of BSND exon 3 is shown (upper panel; SEQ ID NO: 42), together with wild type sequence around the distal breakpoint 579 bp downstream of the stop codon in exon 4 (lower panel; SEQ ID NO: 44) and the cloned junction fragment of affected individual II-1 (middle panel; SEQ ID NO: 43). Equivalent regions of mutant and wild type sequence are encased in boxes. The insert shows in family F708 agarose gel electrophoresis of genomic PCR products of primers del708f and del708r for the wild type allele (3483 bp) and/or the allele (387 bp) harboring the 3096 bp deletion. Lanes represent results from family F708 for the father (F), the mother (M), the two affected children (II-1 and II-2) and a normal control individual (N). Size markers (S) are shown on the left. e, The affected individual of family F662 revealed two heterozygous mutations, a maternal 3G.A transition resulting in loss of the translation initiation codon, together with a paternal 28G.A transition resulting in a non-conservative G10S exchange. The upper panel shows SEQ ID NO: 45 (amino acid) and SEQ ID NO: 47 (nucleic acid) sequences. The lower panel shows SEQ ID NO: 46 (amino acid) and SEQ ID NO: 48 (nucleic acid) sequences. f, The homozygous G23.T transversion in the affected child of family F206 leads to an R8L amino acid exchange. The upper panel shows SEQ ID NO: 49 (amino acid) and SEQ ID NO: 51 (nucleic acid) sequences. The lower panel shows SEQ ID NO: 50 (amino acid) and SEQ ID NO: 52 (nucleic acid) sequences.

Within the 900-kb critical region that contained the cloning gap, the program GENESCAN predicted nine genes, six of which were unknown (FIG. 1e). The putative exons of all nine genes were screened for mutations in affected children from ten BSND families, using single-stranded conformation polymorphism (SSCP) and direct sequencing of exon PCR products and reverse transcription-PCR (RT-PCR) products of cDNA from lymphocytes transformed with Epstein-Barr virus. No mutations were detected. When the sequence from BAC GS 1-118i5 was generated, GENESCAN identified two further putative genes (FIG. 1e). Direct sequencing of PCR products from primers flanking the four exons of one of the two genes revealed seven distinct mutations in the ten BSND families used in haplotype analysis and, in addition, in the Bedouin kindred (F542) in which BSND had first been described (see Table 1; FIG. 6; and Brennan et al., Am. J. Hum. Genet. 62:355-361 (1998)). The gene was named BSND and the gene product barttin. In the consanguineous families, the affected children were homozygous with respect to the mutations. The affected children of families F314, F591, F730, F786 and F791, which originated from Turkey and showed extensive haplotype sharing (FIG. 2), all had an identical mutation. Most mutations detected were loss-of-function mutations, through deletion, loss of splice site or loss of the initiation codon (Table 1 and FIG. 6) were also detected. For mutations that abolish the start site of translation, there were no likely alternative start sites, as methionine codons within the Kozak consensus sites at amino-acid positions 40, 44, 78 and 89 (FIG. 7) were assigned reliability scores between 0.37 and 0.22 only, whereas the score at position 1 was 0.85. A mutation detected in a British kindred was also found in the homozygous state in affected children of the Bedouin kindred F542 (Brennan et al., Am. J. Hum. Genet. 62:355-361 (1998)). The missense mutations affected amino acids 8 and 10 (Table 1), which are conserved between human and mouse (FIG. 7) and are positioned at the border of the first putative membrane-spanning segment, and therefore might have been functionally relevant. All mutations were absent from 92-96 healthy control individuals.

Figure 3:
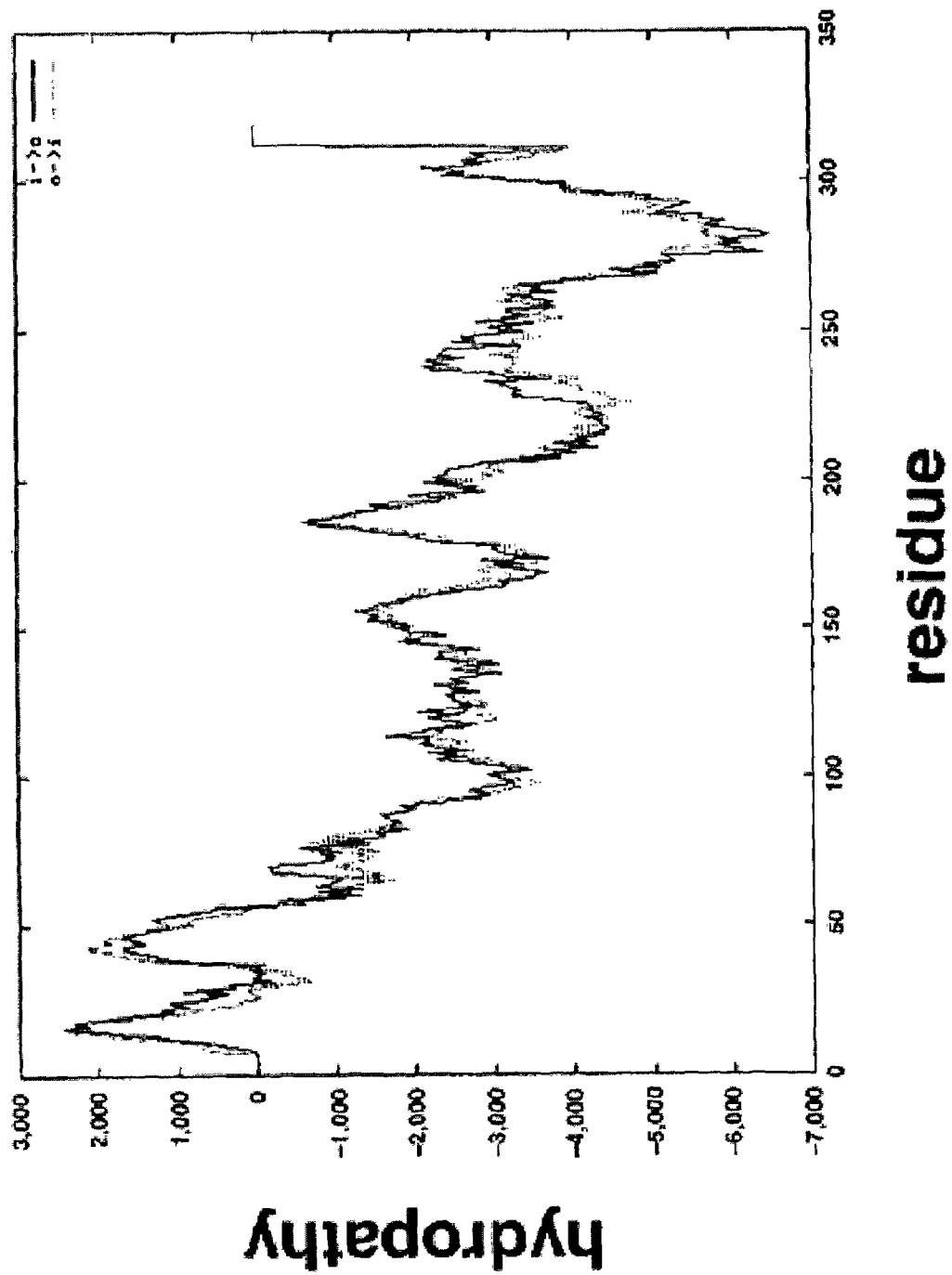
FIG. 3 shows a hydropathy plot for barttin produced by the program TMpred.

BLAST searches of databases, (Altschul et al., Nucleic Acids Research 25:3389-3402 (1997)), using the exon 1 sequence of human BSND as a query yielded the following highly similar expressed sequence tag (EST) clones: two murine ESTs from kidney, one bovine EST from fetal kidney and three human ESTs from renal tumors and one from kidney. The ESTs from both strands were sequenced, except for the bovine EST, which was not available. The human cDNA sequence was 1,596 bp, representing the full-length transcript. The murine CDNA was 2,184 bp long as the result of an extended 3'-untranslated region in the mouse. Within the longest open reading frame of the human cDNA, a start codon was found in a Kozak consensus 63 nt downstream of an in-frame stop codon (FIG. 7). Four exons were identified by sequence alignment of human cDNA to the genomic sequence of BAC clone GS 1-118i5. There was 70% sequence identity between the amino-acid sequences deduced from human and mouse BSND (FIG. 7). All cDNA, genomic and amino-acid sequences of human and murine BSND were compared by BLAST analysis with sequences in pertinent sequence databases, and found no similarities in any of these databases except for the highly similar ESTs from mouse and cow and the human genomic clones described above. Therefore, BSND encoded a hitherto unknown protein. Hydropathy modeling using several programs, including SOSUI and TMpred, predicted two putative membrane-spanning alpha-helices at the amino terminus (FIG. 3). The first alpha-helix was alternatively modeled as a putative signal peptide by the program SMART. Topology algorithms predicted the carboxyl terminus to be inside. No other known domains or motifs were found.

Figure 4:
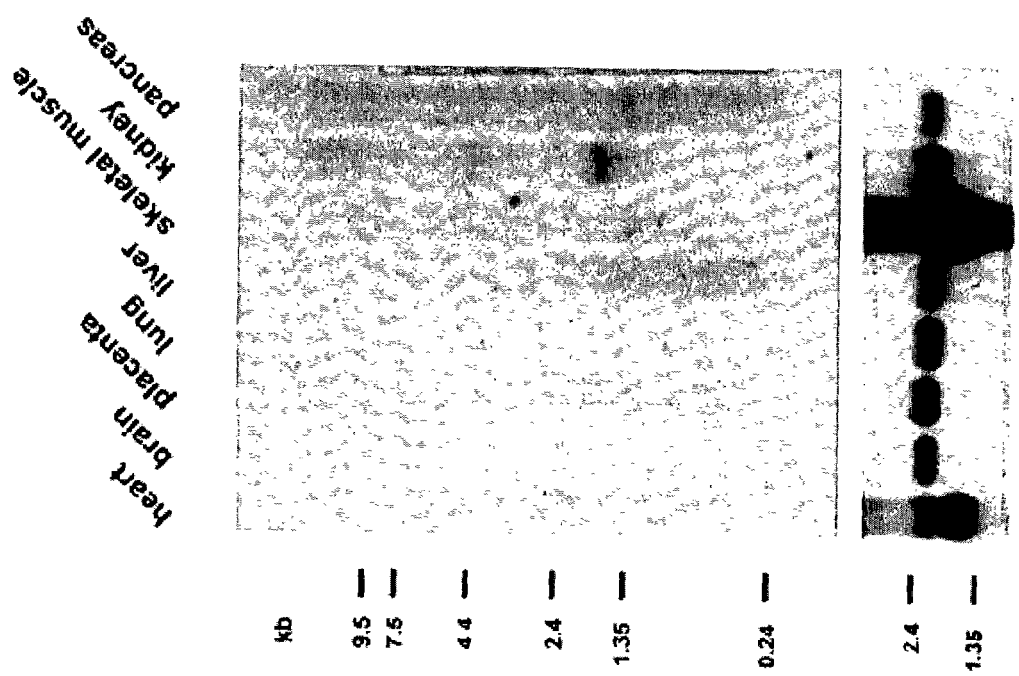
FIG. 4 shows a Northern-blot analysis of the expression pattern of BSND.
Figure 5:
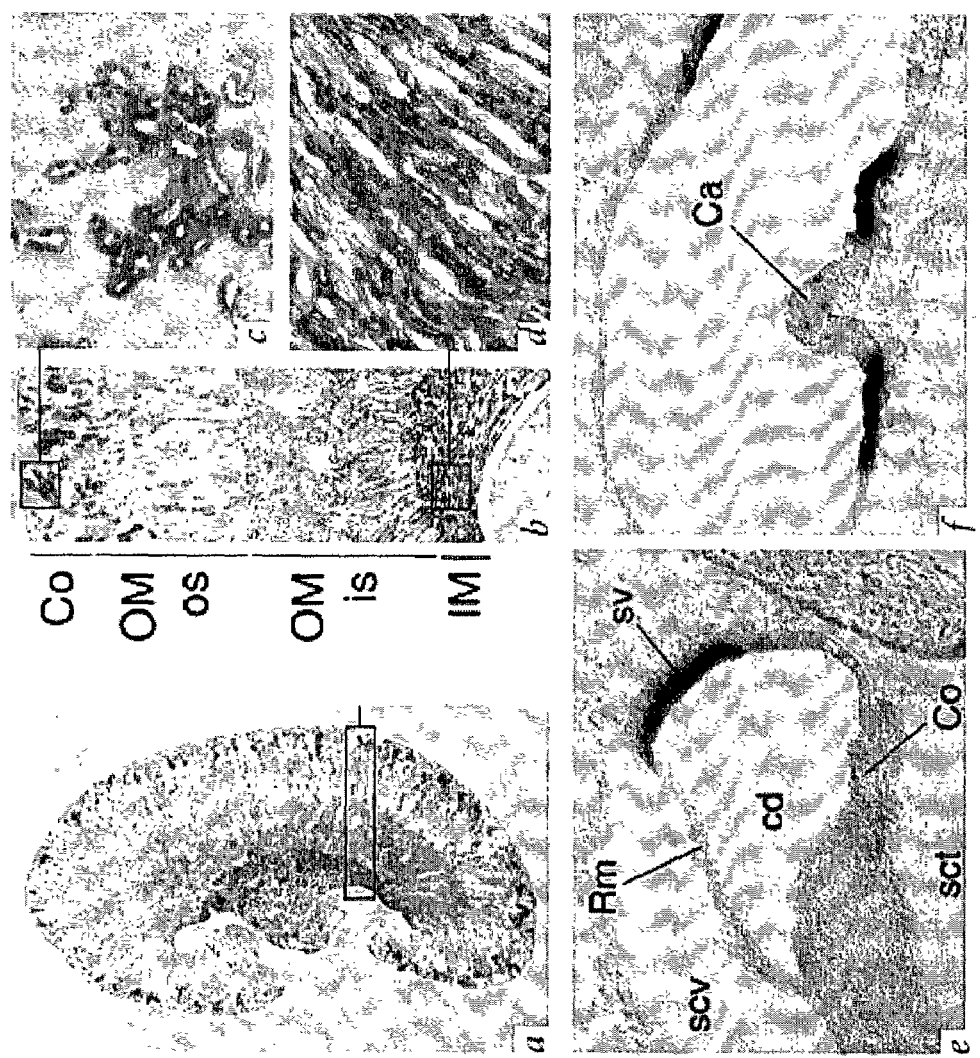
FIG. 5 shows section in situ hybridization analysis of murine Bsnd expression. a, Bsnd expression in a sagittal section of adult mouse kidney. b, Higher magnification of the boxed area in a; the left of the section in a is now to the bottom. c, a subset of renal tubules of the cortex (Co) representing distal convoluted tubules or cortical collecting duct. d, Bsnd expression in the inner medulla. e,f, In situ hybridization of sections of 18.5-dpc fetal mouse inner ear reveals strong and exclusive Bsnd expression in marginal cells of stria vascularis in the cochlea (e) as well as strong expression in dark cells localized at the base of the crista ampullaris of the vestibular organ (f). Ca, crista ampullaris, cd, cochlear duct, Co, organ of Corti, Rm, Reissner membrane, sct, scala tympani, scv, scala vestibuli, sv, stria vascularis.

Northern-blot analysis of several human tissues using a partial BSND cDNA probe yielded a 1.6-kb transcript expressed primarily in human kidney (FIG. 4). The faint additional band at 4.4 kb was most likely to represent incompletely spliced heteronuclear RNA, as no alternative polyadenylation sites or additional exons were identified on scrutiny of genomic and EST sequences. The finding that BSND expression was strongest in kidney was consistent with the prominent renal phenotype of BSND. In situ hybridization analysis was carried out on sections of murine adult kidney. Bsnd shows an expression pattern similar to that of murine NKCC2 (Igarashi et al., Am. J. Physiol. 269:F405-F418 (1995)) and the rat NKCC2 homolog BSC1 (Kaplan et al., Kidney Int., 49:40-47(1996)), as well as to that of rat ClCK2 (FIGS. 5a,b; Yoshikawa et al., Am. J. Physiol. 276:F552-F558 (1999)), encoding the murine and rat Na-K-2Cl cotransporters and the rat ClC-K2 chloride channel, respectively. Expression was evident in inner and outer stripes of the outer medulla of the kidney, most probably representing thin limbs of Henle's loop together with some collecting duct coursing through the outer stripe. In situ hybridization in fetal mouse kidney at 18.5 days post coitum revealed a clear continuity between hybridization signals from the thin limb of Henle's loop and the distal convoluted tubule, suggesting that part of the expression pattern seen in FIG. 5b resulted from expression in the thick ascending limb of Henle's loop. In addition, strong signals were detected in a subset of cortical tubules (Igarashi, et al., Am. J. Physiol. 269:F405-F418 (1995)), representing distal convoluted tubules or cortical collecting duct (FIG. 5c). As the products of all three genes known to be defective in aBS—NKCC2 (Igarashi et al., Am. J. Physiol. 269:F405-F418 (1995)), CLCNKB (Yoshikawa et al., Am. J. Physiol. 276:F552-F558 (1999); Kobayashi et al., J. Am. Soc. Nephrol. 12:1327-1334 (2001)) and ROMK (which encodes an apical inwardly-rectifying Km channel)—were expressed in the thick ascending limbs in mammalian kidney, the Bsnd expression pattern is consistent with the fact that BSND defects result in an aBS phenotype. Strong expression was also observed in the inner medulla of the kidney (FIGS. 5a,b). This expression did not extend all the way to the tip of the papilla (FIG. 5a). Thus this signal most probably represents cells of the thin ascending limbs (FIG. 5d). In this nephron segment, ClCK1, the murine homolog of human CLCNKA, was exclusively expressed (Yoshikawa et al., Am. J. Physiol. 276:F552-F558 (1999)), and has been proposed to play an important part in the urinary concentrating mechanism of the countercurrent system.

Because of the association of aBS with SND in BSND, in situ hybridization of 18.5-dpc fetal mouse cochlea was performed, which revealed strong and exclusive BSND expression in marginal cells of the stria vascularis (FIG. 5e). Several specific cell types surrounding the cochlear duct, including stria vascularis marginal cells and dark cells, were involved in a complex pathway that maintained a high K+ concentration within the cochlear duct (Steel et al., Nature Genetics 27:143-149 (2001)). Genetic defects in several channels and transporters critical for maintenance of high K+ in the endolymph, including KCNQ4 (Kubisch et al., Cell 96:437-446 (1999)), KvLQT1 (Tyson et al., Hum. Mol. Genetics 6:2179-2185 (1997)) and IsK (Kcne1) (Schulze-Bahr et al., Nature Genetics 17:267-268 (1997)), have been implicated in hearing defects (Steel, et al., Nature Genetics 27:143-149 (2001); Petit et al., Nature Genetics 14:385-391 (1996)). An additional link between the renal aBS phenotype and hearing defects in BSND is provided by the fact that furosemide, which inhibits NKCC2 and thereby mimics aBS25, may cause hearing impairment (Delpire et al., Nature Genetics 22:192-195 (1999)). This most probably occurs through inhibition of NKCC1, the secretory isoform of the Na—K-2Cl cotransporter, which has been localized to the basolateral membrane of vestibular dark cells (Delpire et al., Nature Genetics 22:192-195 (1999)) of the mouse inner ear. In addition to the cochlear signal, BSND expression was detected in dark cells localized at the base of the crista ampullaris of the vestibular organ (FIG. 5f). Co-expression of KCNQ1 and KCNE1 have been reported at the apical membrane of this cell type, which is responsible for production of endolymph for the vestibular endolymphatic space through a transport model similar to that for the stria vascularis (Nicolas et al., Hear. Res. 153:132-145 (2001)).

The present invention is not limited to a particular mechanism. Indeed, an understanding of the mechanism of action is not necessary to practice the present invention. Nonetheless, it is contemplated that several mechanistic interpretations may account for the experimental results presented in Example 1. Interpretations include, but are not limited to, the protein barttin may act as a regulator for one of the ion-transport proteins involved in aBS, the protein barttin may represent a transporter, and the protein barttin may represent a channel itself.

TABLE 1

Mutations detected in BSND*

| Family | Origin | Parental consanguinity | Nucleotide change | Effect on coding sequence | Exon |
|---|---|---|---|---|---|
| F314 | Turkey | yes | A1T | loss of START codon | 1 |
| F591 | Turkey | yes | A1T | loss of START codon | 1 |
| F730 | Turkey | yes | A1T | loss of START codon | 1 |
| F786 | Turkey | yes | A1T | loss of START codon | 1 |
| F791 | Turkey | yes | A1T | loss of START codon | 1 |
| F813 | Northern Africa | yes | C22T | R8W | 1 |
| F197 | Northern Africa | yes | 157_IVS1 + 20del41 | loss of splice site | 1 |
| F708 | Lebanon | yes | EX3_EX4del | loss of exons 3 and 4 | 3,4 |
| F662 | UK | no | G3A | loss of START codon | 1 |
|  |  |  | G28A | G10S | 1 |
| F206 | France | yes | G23T | R8L | 1 |
| F542 | Israel | yes | G28A | G10S | 1 |

*In families with parental consanguinity, all mutations were present in the homozygous state in affected individuals and in the heterozygous state in their parents.

EXAMPLE 2

Barttin is a Cl⁻ Channel Beta-Subunit Crucial for Renal Cl⁻ Reabsorption and Inner Ear K⁺ Secretion A. Methods Functional Expression in Xenopus Oocytes.

Capped complementary RNA of CLC channels (10 ng) and barttin (5 ng) were expressed in *Xenopus* oocytes as described (Waldegger et al., J. Biol. Chem. 268:3821-3824 (1993), erratum J. Biol. Chem. 269:19192 (1994)). Mutations were introduced by recombinant PCR and sequenced. Measurements were in ND96 medium (96 mM sodium chloride, 2 mM potassium chloride, 1.8 mM calcium chloride, 1 mM magnesium chloride and 5 MM HEPES buffer at pH 7.4). For anion replacement, 80 mM Cl— was substituted by equivalent amounts of Br—, I— or NO-3. At pH 5.4 or 6.4, HEPES was replaced by 5 mM MES buffer, and at pH 8.4 by 5 mM Tris buffer.

Patch-Clamp Experiments of Transfected Cells.

Patch-clamp experiments of transfected cells tsA201 cells were transiently transfected with complementary DNAs inserted into pCIneo vector with Lipofectamin (Invitrogen). Currents were measured after 2-3 days in the whole-cell mode of the patch-clamp technique using 3-5-M[Omega] pipettes and an Axopatch 200-A amplifier. The bath solution contained 130 mM sodium chloride, 5 mM potassium chloride, 2 mM magnesium chloride, 2 mM calcium chloride and 10 mM HEPES at pH 7.4. For ion selectivity measurements, Cl— was exchanged for Br— or I—. Pipette solutions contained 130 mM caesium chloride, 5 mM sodium chloride, 2 mM calcium chloride, 2 mM magnesium chloride, 10 mM HEPES and 5 mM EGTA at pH 7.4.

Measurement of Surface Expression.

Haemagglutinin (HA) epitopes were introduced between transmembrane domains D8 and D9 of ClC-Ka, ClC-Kb and ClC-1. This did not interfere with their ability to generate currents. Surface expression used HA antibodies and chemiluminescence was as described (Zerangue et al., Neuron 22:537-548 (1999); Schwake et al., J. Biol. Chem. 276: 12049-12054 (2001)).

Antibodies.

Figure 15:
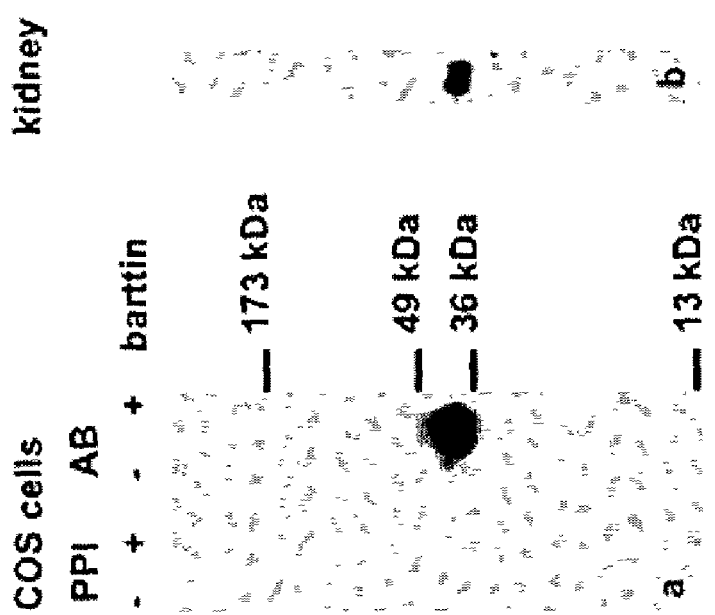
FIG. 15 shows antibodies against barttin.

The generation of rabbit and guinea-pig antisera against barttin is described in FIG. 15. Published antibodies against ClC-K7, KCNQ1 (Dedek et al., Pflugers Arch. Eur. J. Physiol. 442:896-902 (2001), AE1 (Alper et al., Proc. Nat. Acad. Sci. USA 86:5429-5433 (1989)) and aquaporin-2 (Nielson et al., Proc. Natl. Acad. Sci. USA 90:11663-11667 (1993)), and commercial antibodies against ROMK (Chemicon), Tamm-Horsfall protein (Dunn), myc epitope (9E10; American Type Culture Collection, ATCC) and HA epitope (3F10; Roche) were used. Fluorophore-coupled secondary antibodies were from Molecular Probes and Jackson.

Immunohistochemistry.

Anaesthetized adult mice were perfused through the left ventricle with PBS followed by 4% paraformaldehyde (PFA) in PBS. Adult cochlea were decalcified with Rapid Bone Decalcifier (Eurobio). Inner ears from newborn mice were fixed after dissection. Tissue samples were mounted in OCT compound (Tissue Tek) for cryosections or embedded in paraffin and cut to 8-12-µm sections. Sections were fixed in 4% PFA, 0.1% desoxycholate and 0.2% NP40 in PBS, washed, and blocked in 2% BSA, 3% goat serum and 0.5% NP40 in PBS. Antisera were applied in 2% BSA and 0.5% NP40 in PBS. Analysis was by confocal microscopy (Leica).

B. Results

ClC-Ka and ClC-Kb are highly homologous Cl— channels that are nearly exclusively expressed in kidney (Kieferle et al., Proc. Natl. Acad. Sci. USA 91:6943-6947 (1994)). CLCNKB mutations in Bartter's syndrome (Simon et al., Nature Genetics 17:171-178 (1997)) together with immunohistochemical results (Vandewalle et al., Am. J. Physiol. 272:F678-F688 (1997)); Kobayashi et al., J. Am. Soc. Nephrol. 12:1327-1334 (2001)) suggest that human ClC-Kb (the orthologue of rodent ClC-K2) mediates basolateral Cl— efflux in the thick ascending limb of Henle's loop and in more distal nephron segments. Similarly, immunolocalization (Uchida et al., J. Clin. Invest. 95:104-113 (1995)) and the diabetes insipidus observed in Clcnk1$^{-/-}$mice (Matsumura et al., Nature Genetics 21:95-98 (1999)) indicate that rodent ClC-K1 (the orthologue of human ClC-Ka) is crucial for transepithelial transport in the thin ascending limb. Whereas ClC-K1 yields Cl$^-$ currents on heterologous expression (Uchida et al., J. Clin. Invest. 95:104-113 (1995); Waldegger et al., J. Biol. Chem. 276:12049-12054 (2001)) no currents are observed with human ClC-Ka or ClC-Kb6, 12, suggesting that ClC-K channels may need [beta]-subunits.

Figure 8:
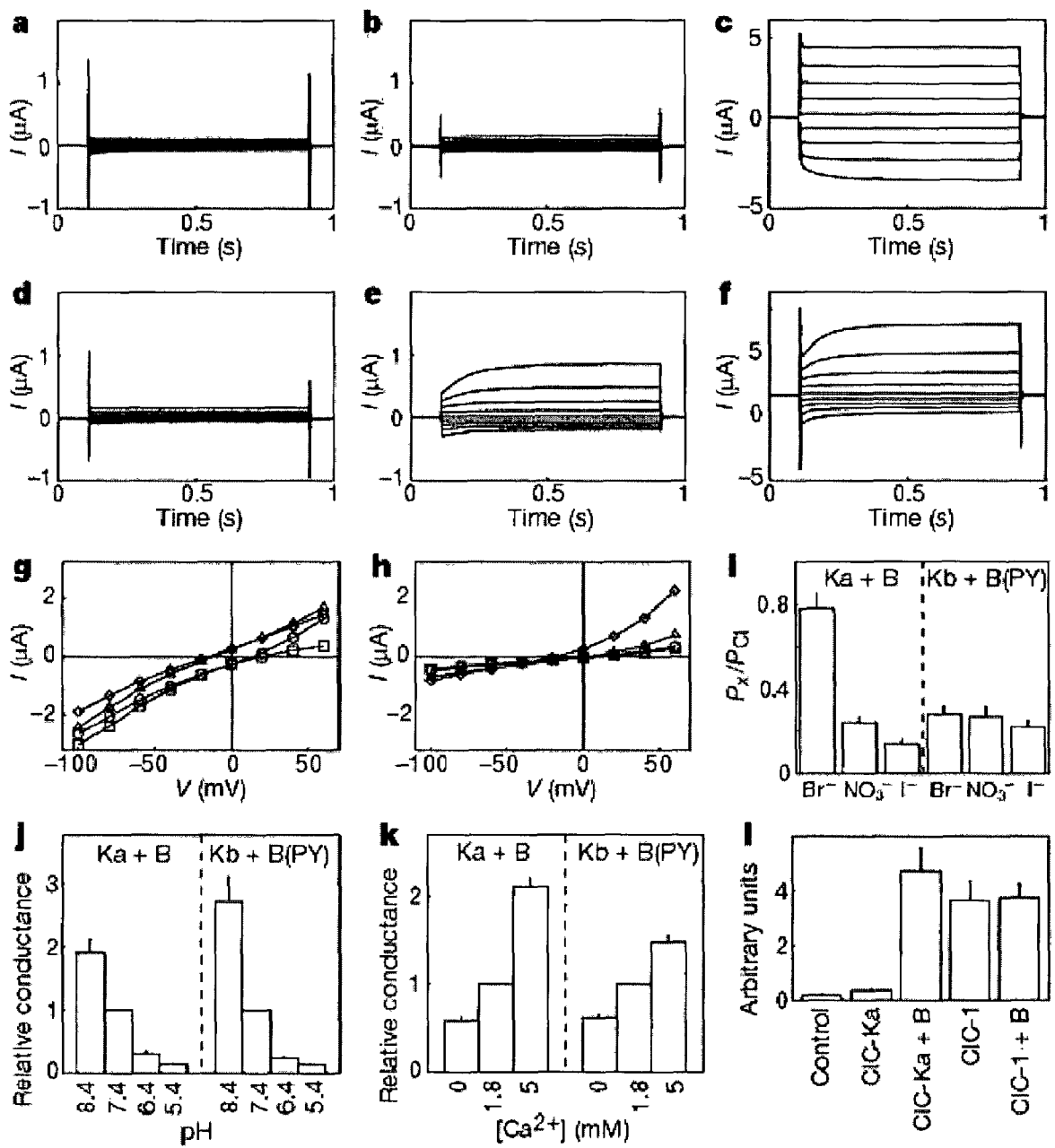
FIG. 8 shows functional characterization of ClC-K/barttin in *Xenopus* oocytes. a-f, Measurements of current (I). Barttin (a), ClC-Ka (b) and ClC-Kb (d) alone gave no significant currents. ClC-Ka/barttin co-expression gave large currents (c), and ClC-Kb/barttin moderate currents (e). f, ClC-Kb/barttin(Y98A) currents. g, h, Steady-state current-voltage relationships for ClC-Ka/barttin and ClC-Kb/barttin(Y98A), respectively, in the presence of: Cl$^-$, diamonds; Br$^-$, triangles; NO$^-_3$, circles; I$^-$, squares. i, Permeability ratios ($P_x/P_{Cl}$) from reversal potentials for ClC-Ka/barttin (left) and ClC-Kb/barttin(Y98A) (right). j, Effect of extracellular pH on ClC-Ka/barttin (left) and ClC-Kb/barttin(Y98A). k, Effect of extracellular Ca$^{2+}$ on ClC-Ka/barttin (left) and ClC-Kb/barttin(Y98A). l, Surface expression[13] of epitope-tagged ClC-Ka. ClC-Ka with a cytoplasmic HA tag (left) and extracellularly tagged ClC-1 served as controls. B, barttin; B(PY), barttin(Y98A).

Positional cloning of the gene BSND, which underlies Bartter's syndrome type 4 (also named BSND; OMIM accession number 602522), identified barttin (Example 1). When barttin was co-expressed with ClC-Ka in *Xenopus* oocytes, large Cl— currents were observed (FIG. 8*c*). No currents were seen with barttin, ClC-Ka or ClC-Kb alone (FIGS. 8*a, b, d*). In oocytes, barttin/ClC-Kb co-expression gave small but detectable currents (FIG. 8*e*). More pronounced effects on ClC-Kb were seen in transfected tsA201 cells (see FIG. 12), and in oocytes injected with an activating mutant of barttin (Y98A; see below) (FIG. 8*f*). In oocytes, voltage activation differed between ClC-Ka/barttin and ClC-Kb/barttin (FIGS. 8*c, e, f*). No such difference was found in mammalian cells (see FIG. 12). Barttin also markedly increased currents of rat ClC-K1, which yields small currents by itself (Uchida et al., J. Clin. Invest. 95:104-113 (1995); Waldegger et al., J. Biol. Chem. 276:12049-12054 (2001); FIG. 9*b*). The effect was specific for ClC-K because currents of ClC-1, ClC-2 and ClC-5 were not changed by barttin (data not shown). Barttin enhanced the surface expression (Zerangue et al., Neuron 22:537-548 (1999); Schwake et al., J. Biol. Chem. 276:12049-12054 (2001)) of ClC-Ka, but not of the muscle channel ClC-1 (FIG. 8).

Ion substitution revealed that both ClC-Ka/barttin and ClC-Kb/barttin were anion selective (FIGS. 8*g-i*). As is typical for the CLC family (Jentsch et al., Pflugers Arch. Eur. J. Physiol. 437:783-795 (1999)), they conducted Cl$^-$ better than I$^-$. Permeability sequences were Cl$^{(-)}$ (greater than or equal to) Br$^-$>NO3$^-$>I$^-$ for ClC-Ka/barttin, and Cl$^-$>Br$^-$=NO3$^-$ (greater than or equal to) I$^-$ for ClC-Kb/barttin (FIG. 8*i*). Heteromeric ClC-K/barttin channels were sensitive to extracellular pH (FIG. 8*j*) and Ca2+ (FIG. 8*k*). The inhibition of ClC-Ka/barttin by low extracellular pH and its stimulation by extracellular Ca2+ compares well to rat ClC-K1 expressed by itself (Uchida et al., J. Clin. Invest. 95:95-98 (1999); Waldegger et al., J. Biol. Chem. 275: 24527-24533 (2000)). Compared with ClC-Ka/barttin, ClC-Kb/barttin was more sensitive to pH and less responsive to Ca2+.

Barttin has two hydrophobic stretches that may span the membrane (Birkenhager et al., Nature Genetics 29:310-314 (2001); FIG. 9*a*). Epitope-tagging experiments supported this model by indicating that the first hydrophobic stretch is not a cleavable signal peptide (see FIG. 13). Consistent with the poor conservation between species of the second half of barttin (Birkenhager et al., Nature Genetics 29:310-314 (2001)), and with the observation that all described disease-causing mutations affect the amino-terminal half (Birkenhager et al., Nature Genetics 29:310-314 (2001)), it was contemplated that large portions of the carboxy terminus could be deleted without abolishing the stimulatory effect on ClC-K1 (FIG. 9*b*). Truncating the protein before residue 85, however, destroyed function. The deleted segment contained a putative PY motif (Staub et al., EMBO J. 15:2371-2380 (1996); Schild et al., EMBO J. 15:2381-2387 (1996); FIG. 9*a*). When the critical tyrosine residue (Schild et al., EMBO J. 15:2381-2387 (1996)) was mutated (Y98A), stimulation of ClC-Ka and ClC-Kb currents by barttin was enhanced (FIGS. 1*f* and 2*c*). Macroscopic currents did not differ qualitatively from those of wild-type heteromers. Because ClC-Kb/barttin currents are small in oocytes, this activating mutant was used to reliably investigate properties of heteromeric ClC-Kb (FIGS. 8*f, h-k*). The effects of this mutation resemble results obtained with the Na+ channel EnaC (Staub et al., EMBO J. 15:2371-2380 (1996); Schild et al., EMBO J. 15:2381-2387 (1996)) and the Cl- channel ClC-5 (Schwake et al., J. Biol. Chem. 276:12049-12054 (2001)). In those cases, the increase in currents depended on an interaction of their PY motifs with WW domains of ubiquitin protein ligases (Schwake et al., J. Biol. Chem. 276:12049-12054 (2001); Staub et al., EMBO J. 16:6325-6336 (1997)).

Figure 10:
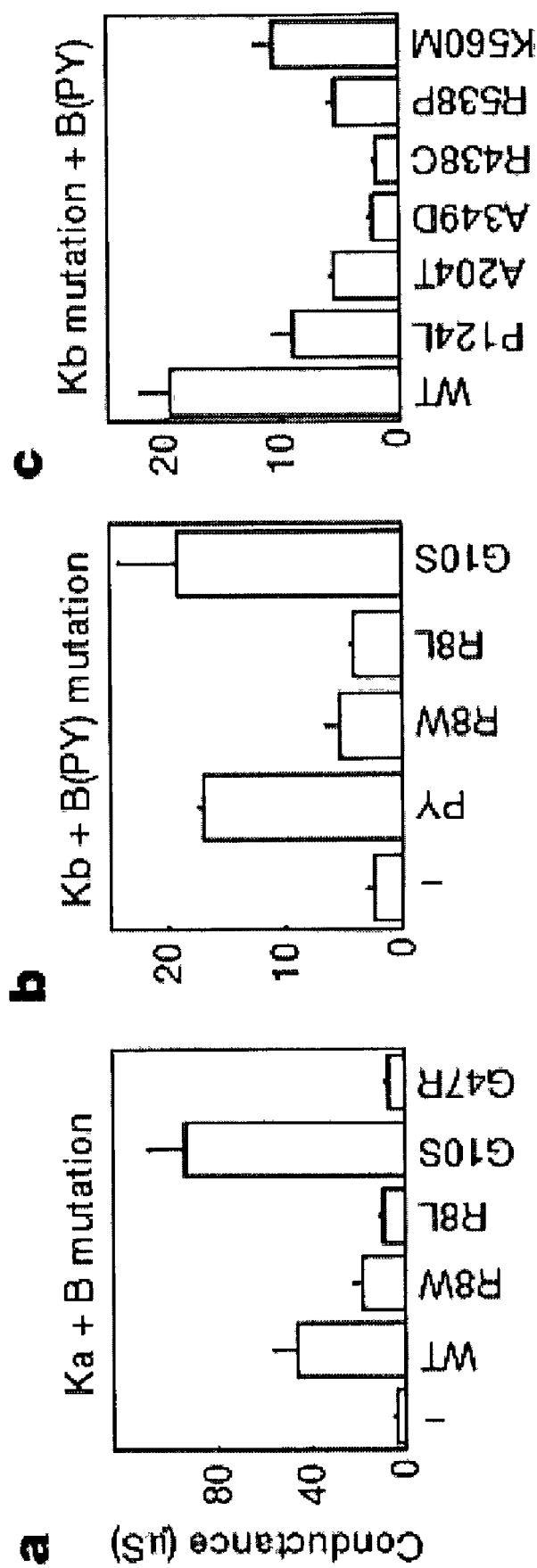
FIG. 10 shows functional consequences of disease-associated mutations in *Xenopus* oocytes. a, b, Effect of barttin (B) missense mutations on ClC-Ka (a) and ClC-Kb (b). c, Effects of CLCNKB missense mutations on ClC-Kb/barttin.

In addition to deletions and truncations, missense mutations in the N-terminal part of barttin (FIG. 9*a*) were associated with BSND (Example 1). Most of these mutations abolished or decreased the stimulatory effect on ClC- Ka or ClC-Kb (FIGS. 10a, b). In the two cases that were investigated (R8L and R8W), the mutated proteins failed to increase surface expression of ClC-Ka. One missense mutation (G10S) increased ClC-Ka currents over those obtained with wild-type barttin, and did not reduce effects on ClC-Kb when studied in the framework of the activating Y98A mutant (FIGS. 10a, b). Disease-causing missense mutations of ClC-Kb (Simon et al., Nature Genetics 17:171-178 (1997); Konrad et al., J. Am. Soc. Nephrol. 11:1449-1459 (2000)) resulted in significant reductions or the loss of ClC-Kb/barttin currents (FIG. 10c).

In situ hybridization showed barttin expression in specific nephron segments and in the stria vascularis (Birkenhager et al., Nature Genetics 29:310-314 (2001)). It was contemplated that if barttin acted as a [beta]-subunit for ClC-Ka and ClC-Kb, than these proteins should colocalize in membranes. Immunofluorescence revealed that all nephron segments expressing barttin also expressed ClC-K proteins and vice versa. As the ClC-K antibody (Vandewalle et al., 272:F678-F688 (1997)) does not distinguish between the highly homologous ClC-K1 and ClC-K2 proteins, this suggests that barttin forms heteromers with ClC-K1 (ClC-Ka) in the thin ascending limb of Henle (Uchida et al., J. Clin. Invest. 95:104-113 (1995)), and with ClC-K2 (ClC-Kb) in the thick ascending limb and more distal segments (Kobayashi et al., J. Am. Soc. Nephrol. 12:1327-1334 (2001)). Staining for barttin and ClC-K was basolateral. The Tamm-Horsfall protein and ROMK K+ channels are expressed in apical membranes of the thick ascending limb, the basolateral membranes of which stained for barttin and ClC-K. Barttin was also detected in basolateral membranes of intercalated cells of the collecting duct, which are known to express ClC-K2 (ClC-Kb) as well (Kobayashi et al., J. Am. Soc. Nephrol. 12:1327-1334 (2001)). On the basis of the (green) staining for the basolateral anion exchanger AE1, which identifies [alpha]-intercalated cells (Alper et al., Proc. Natl. Acad. Sci. USA 86:5429-5433 (1989)), both acid-secreting [alpha]-intercalated cells and base-secreting [beta]-intercalated cells express barttin basolaterally, but intervening aquaporin-2-expressing principal cells (Nielson et al., Proc. Natl. Acad. Sci. USA 90:11663-11667 (1993)) appear devoid of barttin.

In the inner ear, barttin colocalized with ClC-K in K+-secreting marginal cells of the stria vascularis. The basolateral staining for both proteins contrasted with the apical localization of the KCNQ1 K+channel. Previous work (Ando et al., Neurosci. Lett. 284:171-174 (2000)) had identified ClC-K-like currents in marginal cells and correlated them with the presence of ClC-K1 messenger RNA. Experiments with polymerase chain reaction after reverse transcription (RT-PCR) revealed that not only ClC-K1, but also ClC-K2, was expressed in the cochlea (see FIG. 14), indicating that both isoforms are expressed in stria vascularis. Barttin was also found in K+-secreting vestibular dark cells, where it colocalized in basolateral membranes with ClC-K below apical membranes that expressed KCNQ1. No balance problems were reported in BSND, but humans can adapt well to vestibular disturbances (Baloh & Vertigo, Lancet 352:1841-1846 (1998)).

Figure 11:
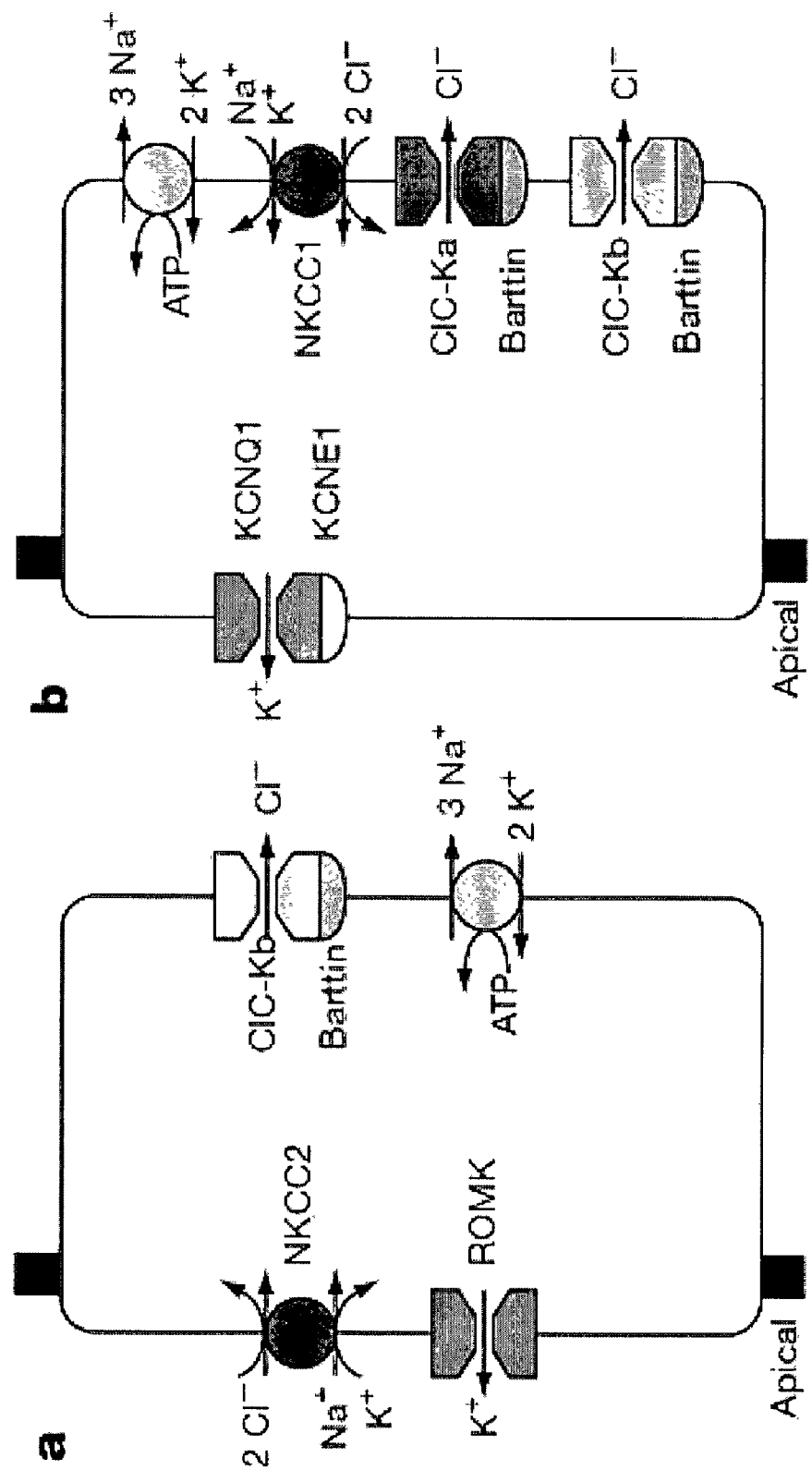
FIG. 11 shows a model for renal Cl$^-$ reabsorption (a), and for K$^+$ secretion in the stria vascularis (b). a, In cells of the renal thick ascending limb, apical NKCC2 cotransporters driving Cl$^-$ uptake require ROMK to recycle K$^+$. Cl$^-$ exits through channels containing ClC-Kb α-subunits and barttin β-subunits. Mutations in all four genes cause Bartter's syndrome. b, In strial marginal cells, basolateral NKCC1 raises intracellular K$^+$ concentration. Parallel ClC-Ka/barttin and ClC-Kb/barttin channels recycle Cl$^-$. K$^+$ exits through channels containing KCNQ1 α-subunits and KCNE1 β-subunits. Loss of KCNQ1, KCNE1, NKCC1 or barttin causes deafness. Neither loss of ClC-K1 (the orthologue of ClC-Ka) nor of ClC-Kb alone entails deafness.

This example describes the identification of a [beta]-subunit for ClC-K Cl- channels. In the kidney, ClC-K/barttin heteromers mediate Cl- reabsorption by facilitating its basolateral efflux (FIG. 11a). In the stria, ClC-K/barttin channels drive K+ secretion by recycling Cl- for the basolateral NKCC1 cotransporter (FIG. 11b). This role is analogous to that of ROMK in Cl—reabsorbing cells of the thick ascending limb, where it recycles K+ for the apical NKCC2 cotransporter (FIG. 11a).

Figure 12:
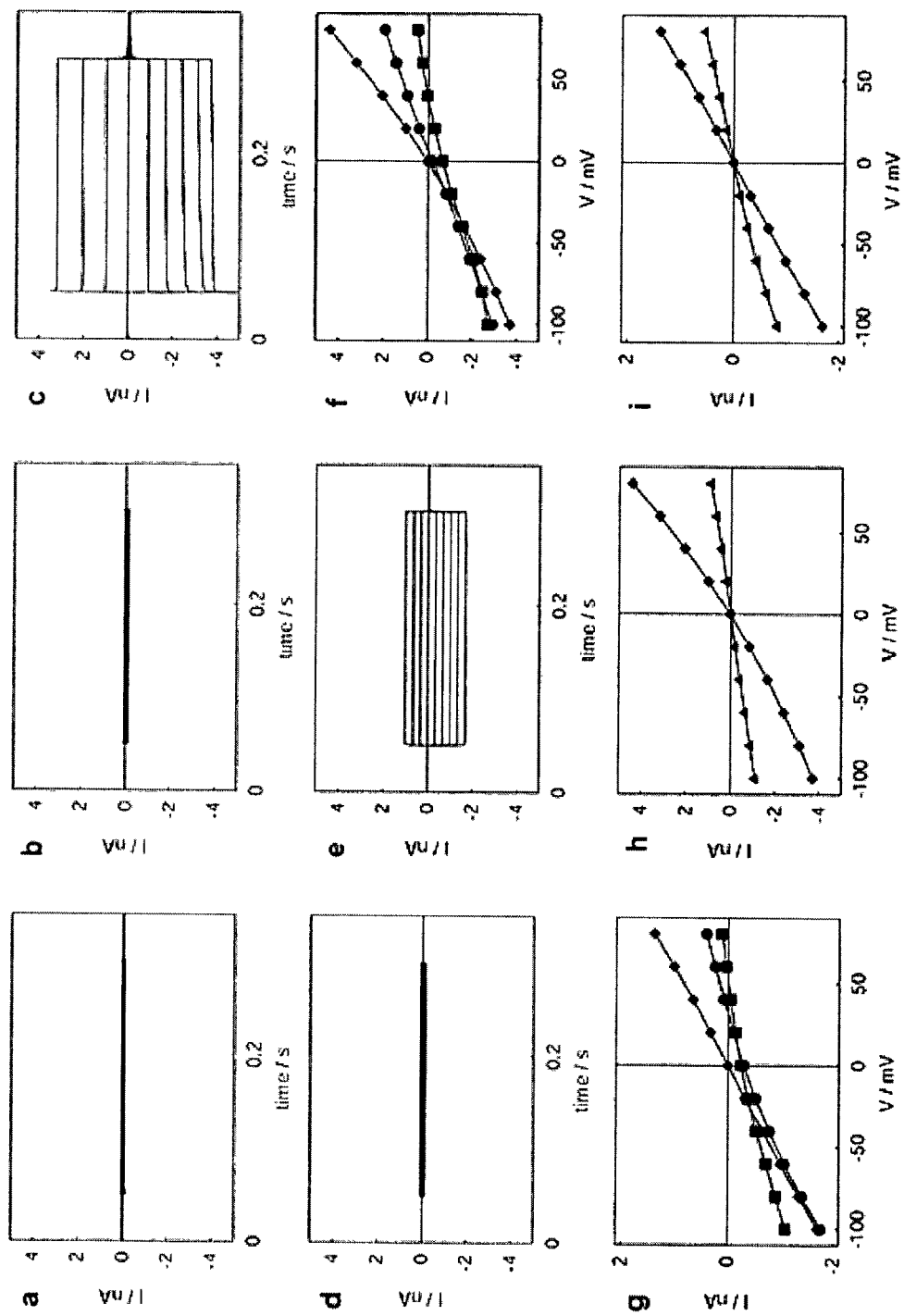
FIG. 12 shows functional characterization of ClC-K/barttin channels expressed in transfected tsA201 cells.
Figure 13:
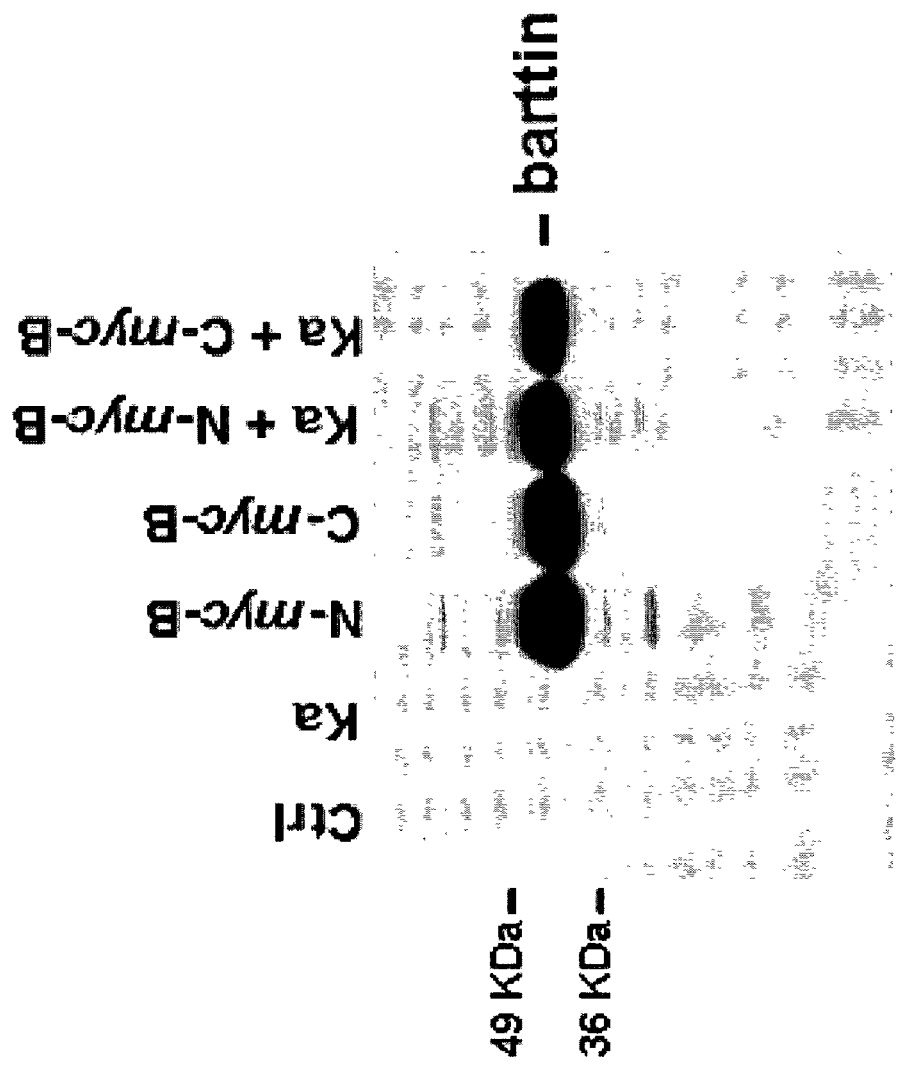
FIG. 13 shows the Topology of barttin.
Figure 14:
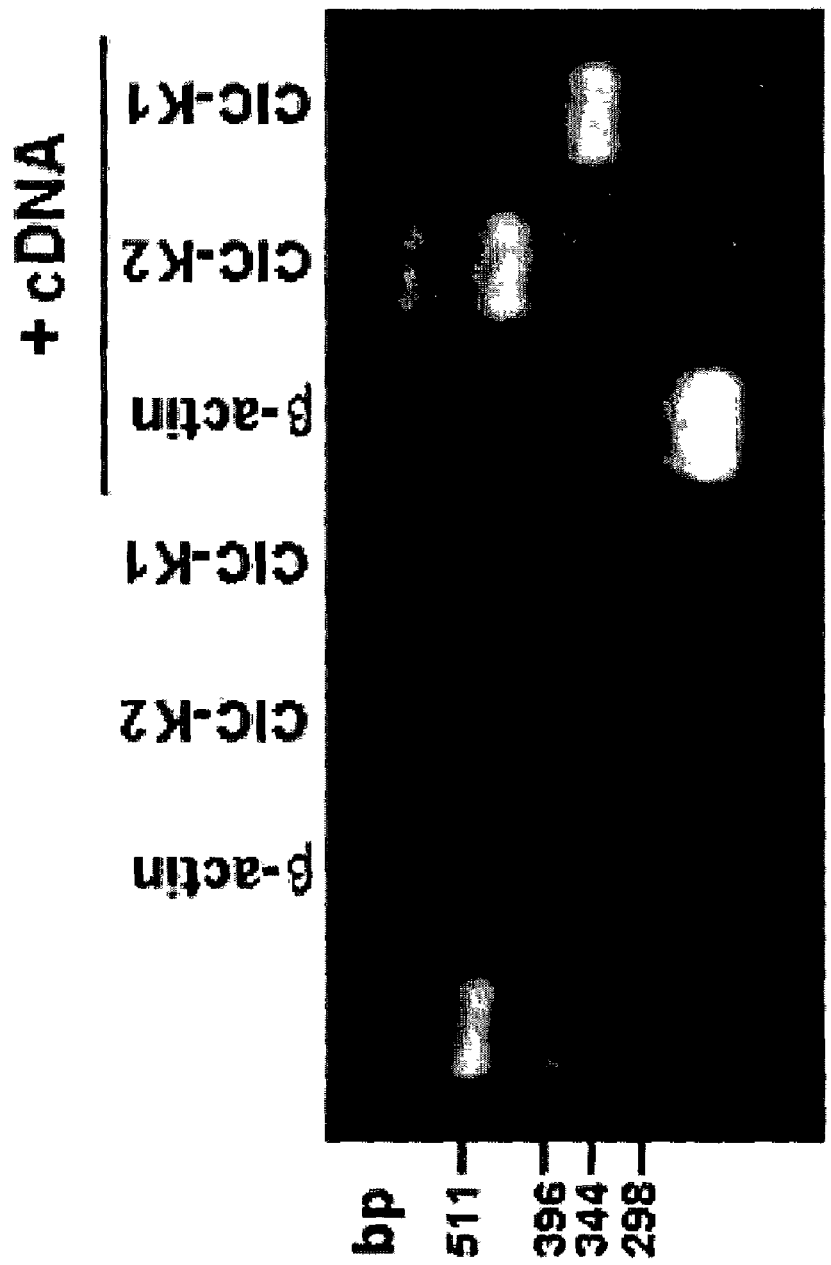
FIG. 14 shows RT-PCT detection of ClC-K1 and ClC-K2 in the cochlea.

FIG. 12 shows functional characterization of ClC-K/barttin channels expressed in transfected tsA201 cells. Barttin (a), ClC-Ka (b), and ClC-Kb (d) did not yield significant currents that were not larger than those from untransfected tsA201 cells. Large currents were seen upon ClC-Ka/barttin co-expression (c). Different from the oocyte system rather large currents were seen upon ClC-Kb/barttin expression (e). FIGS. 12f, g, show steady-state current-voltage relationships in tsA201 cells expressing ClC-Ka/barttin, and ClC-Kb/barttin, respectively, in the presence of different anions. Similar to the oocyte system, in which ClC-Kb/barttin (Y98A) was investigated, Br— is less permeant in ClC-Kb/barttin than in ClC-Ka/barttin. FIG. 13 shows the topology of barttin. The first hydrophobic region of barttin may span the membrane or may act as a cleavable signal peptide. To distinguish between these possibilities, the protein was epitope-tagged at either end. This did not affect its ability to elicit currents with ClC-Ka. When these constructs were expressed in COS cells with or without ClC-Ka (Ka) and analysed by Western blotting using an antibody against the epitope, bands corresponding in size to barttin were stained with comparable intensities irrespective of the position of the epitope (FIG. 13B). This argues against an amino-terminal cleavage, and supports a model in which barttin has two transmembranes spanning segments in its amino-terminal end. FIG. 14 shows RT-PCR detection of ClC-K1 and ClC-K2 in the cochlea. To examine whether ClC-K1 and ClC-K2 is expressed in the cochlea, RT-PCR experiments were performed on RNA obtained from mouse cochlea. The primers used could differentiate between the highly homologous (~90% identity) ClC-K1 and ClC-K2 mRNAs. Using PCR conditions and primers described in reference 24, bands of the correct sizes were observed in samples containing cochlear RNA, but not in controls (FIG. 14C). Thus, both ClC-K1 and ClC-K2 are expressed in the cochlea. Because immunofluorescence indicates that ClC-K channels are only present in the stria vascularis, this strongly suggests that these cells express both isoforms. FIG. 15 shows antibodies against barttin. Polyclonal antisera against barttin were raised in rabbits against the peptide VPADSDFQGIL-SPKA (residues 63-77; SEQ ID NO: 24) and in guinea-pigs against a mixture of the peptides PEQEEEDLYYGLPD (residues 288-301; SEQ ID NO: 25) and LLPDKELGFEP-DIQG (residues 306-320; SEQ ID NO: 26). There were affinity-purified against the corresponding peptides. They were specific as they recognized a band of the expected size only in cells transfected with barttin, but not in non-transfected control cells. In basolateral kidney membranes, only a band of the correct size was detected. Both antibodies, directed against non-overlapping epitopes, detected identical structures in the kidney and the inner ear. Specific staining of the P0 stria vascularis is shows using the rabbit antibody.

The present invention is not limited to a particular mechanism. Indeed, an understanding of the mechanism is not necessary to practice the present invention. Nonetheless, it is contemplated that these experiments may involve several interpreations. An example, which the present invention is not limited to, is that because barttin is crucial for ClC-Kb function, its inactivation results in renal salt wasting as do mutations in ClC-Kb3. However, because barttin also associates with ClC-Ka, additional symptoms are expected. These may resemble the diabetes insipidus-like phenotype observed on disrupting mouse ClC-K1 (Matsumura et al., Nature Genetics 21:95-98 (1999)). BSND patients present with more severe renal symptoms than patients having mutations in ClC-Kb (Jeck et al., Pediatrics 108:E5 (2001)). Unlike mutations in barttin, mutations in the ClC-Kb [alpha]-subunit (Simon et al., Nature Genetics 17:171-178 (1997)) do not cause deafness, nor was deafness described in mice disrupted for ClC-K1 (Matsumura et al., Nature Genetics 21:95-98 (1999)). One proposal, for which the present invention is not limited to, is that both ClC-K1 and ClC-K2 are present in basolateral membranes of K+-secreting marginal cells (FIG. 11b). Whereas a loss of one of these [alpha]-subunits should reduce basolateral recycling of Cl- somewhat, the mutational inactivation of the common [beta]-subunit may abolish recycling completely. As with a disruption of the NKCC1 cotransporter (Delpire et al., Nature Genetics 22:192-195 (1999); Dixon et al., Hum. Mol. Genet. 8:1579-1584 (1999)), or with mutations in either subunit of the apical KCNQ1/KCNE1 K+ channel (Neyroud et al., Nature Genetics 15:186-189 (1997); Schulze-Bahr et al., Nature Genetics 17:267-268 (1997)), the resulting impairment of K+ secretion and endolymph production likely explains the congenital deafness observed in BSND.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. An isolated and purified nucleic acid encoding a barttin protein consisting of the sequence of SEQ ID NO. 2.

2. The nucleic acid sequence of claim 1, wherein said sequence is operably linked to a heterologous promoter.

3. The nucleic acid sequence of claim 1, wherein said sequence is contained within a vector.

4. The nucleic acid sequence of claim 3, wherein said vector is within a host cell.

5. An isolated and purified nucleic acid encoding a barttin protein consisting of the sequence of SEQ ID No. 5.

6. An isolated and purified nucleic acid encoding a barttin protein consisting of the sequence of SEQ ID No. 10.

7. An isolated and purified nucleic acid encoding a barttin protein consisting of the sequence of SEQ ID No. 12.

* * * * *

SEQUENCE LISTING

<160> NUMBER OF SEQ ID NOS: 52

<210> SEQ ID NO 1
<211> LENGTH: 1396
<212> TYPE: DNA
<213> ORGANISM: Homo sapiens

<400> SEQUENCE: 1

```
gagagggcaa ggagtaaagg tggctgggtg tgggtccgtt gaagcgagcc gcctccagcc      60
ctgttgaact ggtgggccca gggactggag cgggattgaa agggatcttg ctctcccttg     120
aagcctcgag ttgcagcgat ttcagtgtct tctctccctg tgtaagcctg tctgggtgtt     180
taggctgaac tacagccacc ccctctcccg ggggtgtgca ggccagggac tggccaggca     240
gccatggctg acgagaagac cttccggatc ggcttcattg tgctggggct tttcctgctg     300
gccctcggta cgttcctcat gagccatgat cggccccagg tctacggcac cttctatgcc     360
atgggcagcg tcatggtgat cggggggcatc atctggagca tgtgccagtg ctaccccaag     420
atcaccttcg tccctgctga ctctgacttt caaggcatcc tctcccaaa ggccatgggc      480 ctgctggaga atgggcttgc tgccgagatg aagagcccca gtcccagcc gcctatgta     540 aggctgtggg aggaagccgc ctatgaccag agcctgcctg acttcagcca catccagatg     600
aaagtcatga gctacagtga ggaccaccgc tccttgctgg ccctgagat ggggcagccg      660 aagctgggaa ccagtgatgg aggagaaggt ggccctggcg acgttcaggc ctggatggag     720
gctgccgtgg tcatccacaa gggctcagac gagagtgaag gggaaagacg cctaactcag     780
agctggcccg gcccctggc ctgtcccag ggccctgccc ccttggcttc cttccaagat      840
gacctggaca tggactccag tgaaggcagc agccccaatg catctccaca tgacagggag     900
gaagcttgtt ccccacaaca ggaacctcag ggctgcaggt gcccgctgga ccgcttccaa     960
gactttgccc tgattgatgc cccaacgttg gaggatgagc cccaagaggg gcagcagtgg    1020
gaaatagccc tgcccaacaa ctggcagcgg tacccaagga caaaggtgga ggagaaggag    1080
gcttcggaca caggtgggga ggaacctgag aaggaagagg aagacctgta ctatgggctg    1140
ccagatggag ccgggacct cctcccggac aaggagctgg gttttgagcc tgacacccaa    1200
ggctgagatg tttgtgctcc gtagcttta gtctggaact gctgctgacc cctgtgtgac    1260
atcacagggc ctcagtttcc ctatttgcaa aatgggatga tatggaggtt caatgagatg    1320
```

```
gtggcatttt gagaatggta agaaatacc cagggagggg atgatgccta aaaaaaaaaa      1380
aaaaaaaaaa aaaaaa                                                     1396
```

<210> SEQ ID NO 2
<211> LENGTH: 320
<212> TYPE: PRT
<213> ORGANISM: Homo sapiens

<400> SEQUENCE: 2

```
Met Ala Asp Glu Lys Thr Phe Arg Ile Gly Phe Ile Val Leu Gly Leu
1               5                  10                  15

Phe Leu Leu Ala Leu Gly Thr Phe Leu Met Ser His Asp Arg Pro Gln
            20                  25                  30

Val Tyr Gly Thr Phe Tyr Ala Met Gly Ser Val Met Ile Gly Gly
        35                  40                  45

Ile Ile Trp Ser Met Cys Gln Cys Tyr Pro Lys Ile Thr Phe Val Pro
    50                  55                  60

Ala Asp Ser Asp Phe Gln Gly Ile Leu Ser Pro Lys Ala Met Gly Leu
65                  70                  75                  80

Leu Glu Asn Gly Leu Ala Ala Glu Met Lys Ser Pro Ser Pro Gln Pro
                85                  90                  95

Pro Tyr Val Arg Leu Trp Glu Glu Ala Ala Tyr Asp Gln Ser Leu Pro
            100                 105                 110

Asp Phe Ser His Ile Gln Met Lys Val Met Ser Tyr Ser Glu Asp His
        115                 120                 125

Arg Ser Leu Leu Ala Pro Glu Met Gly Gln Pro Lys Leu Gly Thr Ser
    130                 135                 140

Asp Gly Gly Glu Gly Gly Pro Gly Asp Val Gln Ala Trp Met Glu Ala
145                 150                 155                 160

Ala Val Val Ile His Lys Gly Ser Asp Glu Ser Glu Gly Glu Arg Arg
                165                 170                 175

Leu Thr Gln Ser Trp Pro Gly Pro Leu Ala Cys Pro Gln Gly Pro Ala
            180                 185                 190

Pro Leu Ala Ser Phe Gln Asp Asp Leu Asp Met Asp Ser Ser Glu Gly
        195                 200                 205

Ser Ser Pro Asn Ala Ser Pro His Asp Arg Glu Glu Ala Cys Ser Pro
    210                 215                 220

Gln Gln Glu Pro Gln Gly Cys Arg Cys Pro Leu Asp Arg Phe Gln Asp
225                 230                 235                 240

Phe Ala Leu Ile Asp Ala Pro Thr Leu Glu Asp Glu Pro Gln Glu Gly
                245                 250                 255

Gln Gln Trp Glu Ile Ala Leu Pro Asn Asn Trp Gln Arg Tyr Pro Arg
            260                 265                 270

Thr Lys Val Glu Glu Lys Glu Ala Ser Asp Thr Gly Gly Glu Pro
        275                 280                 285

Glu Lys Glu Glu Glu Asp Leu Tyr Tyr Gly Leu Pro Asp Gly Ala Gly
    290                 295                 300

Asp Leu Leu Pro Asp Lys Glu Leu Gly Phe Glu Pro Asp Thr Gln Gly
305                 310                 315                 320
```

<210> SEQ ID NO 3
<211> LENGTH: 1396
<212> TYPE: DNA
<213> ORGANISM: Homo sapiens

<400> SEQUENCE: 3

```
gagagggcaa ggagtaaagg tggctgggtg tgggtccgtt gaagcgagcc gcctccagcc        60
ctgttgaact ggtgggccca gggactggag cgggattgaa agggatcttg ctctcccttg       120
aagcctcgag ttgcagcgat ttcagtgtct tctctccctg tgtaagcctg tctgggtgtt       180
taggctgaac tacagccacc ccctctcccg ggggtgtgca ggccagggac tggccaggca       240
gccttggctg acgagaagac cttccggatc ggcttcattg tgctggggct tttcctgctg       300
gccctcggta cgttcctcat gagccatgat cggccccagg tctacggcac cttctatgcc       360
atgggcagcg tcatggtgat cggggggcatc atctggagca tgtgccagtg ctaccccaag       420
atcaccttcg tccctgctga ctctgacttt caaggcatcc tctcccccaaa ggccatgggc       480
ctgctggaga atgggcttgc tgccgagatg aagagcccca gtccccagcc gccctatgta       540
aggctgtggg aggaagccgc ctatgaccag agcctgcctg acttcagcca catccagatg       600
aaagtcatga gctacagtga ggaccaccgc tccttgctgg cccctgagat ggggcagccg       660
aagctgggaa ccagtgatgg aggagaaggt ggccctggcg acgttcaggc ctggatggag       720
gctgccgtgg tcatccacaa gggctcagac gagagtgaag gggaaagacg cctaactcag       780
agctggcccg gccccctggc ctgtccccag ggccctgccc ccttggcttc cttccaagat       840
gacctggaca tggactccag tgaaggcagc agccccaatg catctccaca tgacagggag       900
gaagcttgtt ccccacaaca ggaacctcag ggctgcaggt gcccgctgga ccgcttccaa       960
gactttgccc tgattgatgc cccaacgttg gaggatgagc cccaagaggg gcagcagtgg      1020
gaaatagccc tgcccaacaa ctggcagcgg tacccaagga caaaggtgga ggagaaggag      1080
gcttcggaca caggtgggga ggaacctgag aaggaagagg aagacctgta ctatgggctg      1140
ccagatggag ccggggacct cctcccggac aaggagctgg gttttgagcc tgacacccaa      1200
ggctgagatg tttgtgctcc gtagctttta gtctggaact gctgctgacc cctgtgtgac      1260
atcacagggc ctcagtttcc ctatttgcaa aatgggatga tatggaggtt caatgagatg      1320
gtggcatttt gagaatggta aagaaatacc cagggagggg atgatgccta aaaaaaaaaa      1380
aaaaaaaaaa aaaaaa                                                      1396
```

<210> SEQ ID NO 4
<211> LENGTH: 1396
<212> TYPE: DNA
<213> ORGANISM: Homo sapiens

<400> SEQUENCE: 4

```
gagagggcaa ggagtaaagg tggctgggtg tgggtccgtt gaagcgagcc gcctccagcc        60
ctgttgaact ggtgggccca gggactggag cgggattgaa agggatcttg ctctcccttg       120
aagcctcgag ttgcagcgat ttcagtgtct tctctccctg tgtaagcctg tctgggtgtt       180
taggctgaac tacagccacc ccctctcccg ggggtgtgca ggccagggac tggccaggca       240
gccatggctg acgagaagac cttctggatc ggcttcattg tgctggggct tttcctgctg       300
gccctcggta cgttcctcat gagccatgat cggccccagg tctacggcac cttctatgcc       360
atgggcagcg tcatggtgat cggggggcatc atctggagca tgtgccagtg ctaccccaag       420
atcaccttcg tccctgctga ctctgacttt caaggcatcc tctcccccaaa ggccatgggc       480
ctgctggaga atgggcttgc tgccgagatg aagagcccca gtccccagcc gccctatgta       540
aggctgtggg aggaagccgc ctatgaccag agcctgcctg acttcagcca catccagatg       600
aaagtcatga gctacagtga ggaccaccgc tccttgctgg cccctgagat ggggcagccg       660
```

-continued

```
aagctgggaa ccagtgatgg aggagaaggt ggccctggcg acgttcaggc ctggatggag      720
gctgccgtgg tcatccacaa gggctcagac gagagtgaag gggaagacg cctaactcag       780 agctggcccg gccccctggc ctgtccccag ggccctgccc ccttggcttc cttccaagat      840
gacctggaca tggactccag tgaaggcagc agccccaatg catctccaca tgacagggag      900
gaagcttgtt ccccacaaca ggaacctcag ggctgcaggt gcccgctgga ccgcttccaa      960
gactttgccc tgattgatgc cccaacgttg gaggatgagc cccaagaggg gcagcagtgg     1020
gaaatagccc tgcccaacaa ctggcagcgg tacccaagga caaaggtgga ggagaaggag     1080
gcttcggaca caggtgggga ggaacctgag aaggaagagg aagacctgta ctatgggctg     1140
ccagatggag ccggggacct cctcccggac aaggagctgg gttttgagcc tgacacccaa     1200
ggctgagatg tttgtgctcc gtagctttta gtctggaact gctgctgacc cctgtgtgac     1260
atcacagggc ctcagtttcc ctatttgcaa aatgggatga tatggaggtt caatgagatg     1320
gtggcatttt gagaatggta agaaatacc cagggagggg atgatgccta aaaaaaaaa      1380 aaaaaaaaaa aaaaa                                                      1396
```

<210> SEQ ID NO 5
<211> LENGTH: 320
<212> TYPE: PRT
<213> ORGANISM: Homo sapiens

<400> SEQUENCE: 5

```
Met Ala Asp Glu Lys Thr Phe Trp Ile Gly Phe Ile Val Leu Gly Leu
1               5                   10                  15

Phe Leu Leu Ala Leu Gly Thr Phe Leu Met Ser His Asp Arg Pro Gln
                20                  25                  30

Val Tyr Gly Thr Phe Tyr Ala Met Gly Ser Val Met Ile Gly Gly
        35                  40                  45

Ile Ile Trp Ser Met Cys Gln Cys Tyr Pro Lys Ile Thr Phe Val Pro
    50                  55                  60

Ala Asp Ser Asp Phe Gln Gly Ile Leu Ser Pro Lys Ala Met Gly Leu
65                  70                  75                  80

Leu Glu Asn Gly Leu Ala Ala Glu Met Lys Ser Pro Ser Pro Gln Pro
                85                  90                  95

Pro Tyr Val Arg Leu Trp Glu Ala Ala Tyr Asp Gln Ser Leu Pro
            100                 105                 110

Asp Phe Ser His Ile Gln Met Lys Val Met Ser Tyr Ser Glu Asp His
        115                 120                 125

Arg Ser Leu Leu Ala Pro Glu Met Gly Gln Pro Lys Leu Gly Thr Ser
    130                 135                 140

Asp Gly Gly Glu Gly Gly Pro Gly Asp Val Gln Ala Trp Met Glu Ala
145                 150                 155                 160

Ala Val Val Ile His Lys Gly Ser Asp Glu Ser Gly Glu Arg Arg
                165                 170                 175

Leu Thr Gln Ser Trp Pro Gly Pro Leu Ala Cys Pro Gln Gly Pro Ala
            180                 185                 190

Pro Leu Ala Ser Phe Gln Asp Asp Leu Asp Met Asp Ser Ser Glu Gly
        195                 200                 205

Ser Ser Pro Asn Ala Ser Pro His Asp Arg Glu Glu Ala Cys Ser Pro
    210                 215                 220

Gln Gln Glu Pro Gln Gly Cys Arg Cys Pro Leu Asp Arg Phe Gln Asp
225                 230                 235                 240
```

```
Phe Ala Leu Ile Asp Ala Pro Thr Leu Glu Asp Glu Pro Gln Glu Gly
                245                 250                 255

Gln Gln Trp Glu Ile Ala Leu Pro Asn Asn Trp Gln Arg Tyr Pro Arg
            260                 265                 270

Thr Lys Val Glu Glu Lys Glu Ala Ser Asp Thr Gly Gly Glu Glu Pro
        275                 280                 285

Glu Lys Glu Glu Asp Leu Tyr Tyr Gly Leu Pro Asp Gly Ala Gly
    290                 295                 300

Asp Leu Leu Pro Asp Lys Glu Leu Gly Phe Glu Pro Asp Thr Gln Gly
305                 310                 315                 320

<210> SEQ ID NO 6
<211> LENGTH: 1376
<212> TYPE: DNA
<213> ORGANISM: Homo sapiens

<400> SEQUENCE: 6
gagagggcaa ggagtaaagg tggctgggtg tgggtccgtt gaagcgagcc gcctccagcc     60
ctgttgaact ggtgggccca gggactggag cggattgaa agggatcttg ctctcccttg    120
aagcctcgag ttgcagcgat tcagtgtct tctctccctg tgtaagcctg tctgggtgtt    180
taggctgaac tacagccacc ccctctcccg ggggtgtgca ggccagggac tggccaggca    240
gccatggctg acgagaagac cttccggatc ggcttcattg tgctggggct tttcctgctg    300
gccctcggta cgttcctcat gagccatgat cggccccagg tctacggcac cttctatgcc    360
atgggcagcg tcatggtgat cgggggcatc atctggagcg atcaccttcg tccctgctga    420
ctctgacttt caaggcatcc tctccccaaa ggccatgggc ctgctggaga atgggcttgc    480
tgccgagatg aagagcccca gtccccagcc gccctatgta aggctgtggg aggaagccgc    540
ctatgaccag agcctgcctg acttcagcca catccagatg aaagtcatga gctacagtga    600
ggaccaccgc tccttgctgg cccctgagat ggggcagccg aagctgggaa ccagtgatgg    660
aggagaaggt ggccctggcg acgttcaggc ctggatggag gctgccgtgg tcatccacaa    720
gggctcagac gagagtgaag gggaaagacg cctaactcag agctggcccg gccccctggc    780
ctgtccccag gccctgcccc cttggcttc cttccaagat gacctggaca tggactccag    840
tgaaggcagc agcccaatg catctccaca tgacaggag gaagcttgtt ccccacaaca    900
ggaacctcag gctgcaggt gcccgctgga ccgcttccaa gactttgccc tgattgatgc    960
cccaacgttg gaggatgagc cccaagaggg gcagcagtgg gaaatagccc tgcccaacaa   1020
ctggcagcgg tacccaagga caaaggtgga ggagaaggag gcttcggaca caggtgggga   1080
ggaacctgag aaggaagagg aagacctgta ctatgggctg ccagatggag ccggggacct   1140
cctcccggac aaggagctgg gttttgagcc tgacacccaa ggctgagatg tttgtgctcc   1200
gtagctttta gtctggaact gctgctgacc cctgtgtgac atcacagggc tcagtttcc   1260 ctatttgcaa aatgggatga tatggaggtt caatgagatg gtggcatttt gagaatggta   1320
aagaaatacc cagggagggg atgatgccta aaaaaaaaa aaaaaaaaa aaaaaa         1376

<210> SEQ ID NO 7
<211> LENGTH: 515
<212> TYPE: DNA
<213> ORGANISM: Homo sapiens

<400> SEQUENCE: 7
gagagggcaa ggagtaaagg tggctgggtg tgggtccgtt gaagcgagcc gcctccagcc     60
```

```
ctgttgaact ggtgggccca gggactggag cgggattgaa agggatcttg ctctcccttg    120
aagcctcgag ttgcagcgat ttcagtgtct tctctccctg tgtaagcctg tctgggtgtt    180
taggctgaac tacagccacc ccctctcccg ggggtgtgca ggccagggac tggccaggca    240
gccatggctg acgagaagac cttccggatc ggcttcattg tgctggggct tttcctgctg    300
gccctcggta cgttcctcat gagccatgat cggccccagg tctacggcac cttctatgcc    360
atgggcagcg tcatggtgat cgggggcatc atctggagca tgtgccagtg ctaccccaag    420
atcaccttcg tccctgctga ctctgacttt caaggcatcc tctccccaaa ggccatgggc    480
ctgctggaga atgggcttgc tgccgagatg aagag                              515

<210> SEQ ID NO 8
<211> LENGTH: 1396
<212> TYPE: DNA
<213> ORGANISM: Homo sapiens

<400> SEQUENCE: 8
gagagggcaa ggagtaaagg tggctgggtg tgggtccgtt gaagcgagcc gcctccagcc     60
ctgttgaact ggtgggccca gggactggag cgggattgaa agggatcttg ctctcccttg    120
aagcctcgag ttgcagcgat ttcagtgtct tctctccctg tgtaagcctg tctgggtgtt    180
taggctgaac tacagccacc ccctctcccg ggggtgtgca ggccagggac tggccaggca    240
gccatagctg acgagaagac cttccggatc ggcttcattg tgctggggct tttcctgctg    300
gccctcggta cgttcctcat gagccatgat cggccccagg tctacggcac cttctatgcc    360
atgggcagcg tcatggtgat cgggggcatc atctggagca tgtgccagtg ctaccccaag    420
atcaccttcg tccctgctga ctctgacttt caaggcatcc tctccccaaa ggccatgggc    480
ctgctggaga atgggcttgc tgccgagatg aagagcccca gtccccagcc gccctatgta    540
aggctgtggg aggaagccgc ctatgaccag agcctgcctg acttcagcca catccagatg    600
aaagtcatga gctacagtga ggaccaccgc tccttgctgg cccctgagat ggggcagccg    660
aagctgggaa ccagtgatgg aggagaaggt ggccctggcg acgttcaggc ctggatggag    720
gctgccgtgg tcatccacaa gggctcagac gagagtgaag gggaaagacg cctaactcag    780
agctggcccg gccccctggc ctgtcccag ggccctgccc ccttggcttc cttccaagat    840
gacctggaca tggactccag tgaaggcagc agccccaatg catctccaca tgacagggag    900
gaagcttgtt ccccacaaca ggaacctcag ggctgcaggt gcccgctgga ccgcttccaa    960
gactttgccc tgattgatgc cccaacgttg gaggatgagc cccaagaggg gcagcagtgg   1020
gaaatagccc tgcccaacaa ctggcagcgg tacccaagga caaaggtgga ggagaaggag   1080
gcttcggaca caggtgggga ggaacctgag aaggaagagg aagacctgta ctatgggctg   1140
ccagatggag ccgggaccct cctcccggac aaggagctgg gttttgagcc tgacacccaa   1200
ggctgagatg tttgtgctcc gtagctttta gtctggaact gctgctgacc cctgtgtgac   1260
atcacagggc ctcagtttcc ctatttgcaa aatgggatga tatggaggtt caatgagatg   1320
gtggcatttt gagaatggta aagaaatacc cagggagggg atgatgccta aaaaaaaaa    1380 aaaaaaaaaa aaaaaa                                                  1396

<210> SEQ ID NO 9
<211> LENGTH: 1396
<212> TYPE: DNA
<213> ORGANISM: Homo sapiens
```

<400> SEQUENCE: 9

```
gagagggcaa ggagtaaagg tggctgggtg tgggtccgtt gaagcgagcc gcctccagcc      60
ctgttgaact ggtgggccca gggactggag cgggattgaa agggatcttg ctctcccttg     120
aagcctcgag ttgcagcgat ttcagtgtct tctctccctg tgtaagcctg tctgggtgtt     180
taggctgaac tacagccacc ccctctcccg ggggtgtgca ggccagggac tggccaggca     240
gccatggctg acgagaagac cttccggatc agcttcattg tgctggggct tttcctgctg     300
gccctcggta cgttcctcat gagccatgat cggccccagg tctacggcac cttctatgcc     360
atgggcagcg tcatggtgat cggggggcatc atctggagca tgtgccagtg ctaccccaag     420
atcaccttcg tccctgctga ctctgacttt caaggcatcc tctccccaaa ggccatgggc     480
ctgctggaga tgggcttgc tgccgagatg aagagcccca gtccccagcc gcccttatgta     540
aggctgtggg aggaagccgc ctatgaccag agcctgcctg acttcagcca catccagatg     600
aaagtcatga gctacagtga ggaccaccgc tccttgctgg cccctgagat ggggcagccg     660
aagctgggaa ccagtgatgg aggagaaggt ggccctggcg acgttcaggc ctggatggag     720
gctgccgtgg tcatccacaa gggctcagac gagagtgaag gggaaagacg cctaactcag     780
agctggcccg gccccctggc ctgtccccag ggccctgccc ccttggcttc cttccaagat     840
gacctggaca tggactccag tgaaggcagc agccccaatg catctccaca tgacagggag     900
gaagcttgtt ccccacaaca ggaacctcag ggctgcaggt gcccgctgga ccgcttccaa     960
gactttgccc tgattgatgc cccaacgttg gaggatgagc cccaagaggg gcagcagtgg    1020
gaaatagccc tgcccaacaa ctggcagcgg tacccaagga caaaggtgga ggagaaggag    1080
gcttcggaca caggtgggga ggaacctgag aaggaagagg aagacctgta ctatgggctg    1140
ccagatggag ccggggacct cctcccggac aaggagctgg gttttgagcc tgacacccaa    1200
ggctgagatg tttgtgctcc gtagcttttta gtctggaact gctgctgacc cctgtgtgac    1260
atcacaggc ctcagtttcc ctatttgcaa aatgggatga tatggaggtt caatgagatg    1320
gtggcatttt gagaatggta agaaatacc cagggagggg atgatgccta aaaaaaaaa    1380
aaaaaaaaaa aaaaaa                                                    1396
```

<210> SEQ ID NO 10
<211> LENGTH: 320
<212> TYPE: PRT
<213> ORGANISM: Homo sapiens

<400> SEQUENCE: 10

```
Met Ala Asp Glu Lys Thr Phe Arg Ile Ser Phe Ile Val Leu Gly Leu
1               5                   10                  15

Phe Leu Leu Ala Leu Gly Thr Phe Leu Met Ser His Asp Arg Pro Gln
            20                  25                  30

Val Tyr Gly Thr Phe Tyr Ala Met Gly Ser Val Met Val Ile Gly Gly
        35                  40                  45

Ile Ile Trp Ser Met Cys Gln Cys Tyr Pro Lys Ile Thr Phe Val Pro
    50                  55                  60

Ala Asp Ser Asp Phe Gln Gly Ile Leu Ser Pro Lys Ala Met Gly Leu
65                  70                  75                  80

Leu Glu Asn Gly Leu Ala Ala Glu Met Lys Ser Pro Ser Pro Gln Pro
                85                  90                  95

Pro Tyr Val Arg Leu Trp Glu Glu Ala Ala Tyr Asp Gln Ser Leu Pro
            100                 105                 110
```

```
Asp Phe Ser His Ile Gln Met Lys Val Met Ser Tyr Ser Glu Asp His
        115                 120                 125

Arg Ser Leu Leu Ala Pro Glu Met Gly Gln Pro Lys Leu Gly Thr Ser
    130                 135                 140

Asp Gly Gly Glu Gly Gly Pro Gly Asp Val Gln Ala Trp Met Glu Ala
145                 150                 155                 160

Ala Val Val Ile His Lys Gly Ser Asp Glu Ser Glu Gly Glu Arg Arg
                165                 170                 175

Leu Thr Gln Ser Trp Pro Gly Pro Leu Ala Cys Pro Gln Gly Pro Ala
            180                 185                 190

Pro Leu Ala Ser Phe Gln Asp Asp Leu Asp Met Asp Ser Ser Glu Gly
        195                 200                 205

Ser Ser Pro Asn Ala Ser Pro His Asp Arg Glu Glu Ala Cys Ser Pro
    210                 215                 220

Gln Gln Glu Pro Gln Gly Cys Arg Cys Pro Leu Asp Arg Phe Gln Asp
225                 230                 235                 240

Phe Ala Leu Ile Asp Ala Pro Thr Leu Glu Asp Glu Pro Gln Glu Gly
                245                 250                 255

Gln Gln Trp Glu Ile Ala Leu Pro Asn Asn Trp Gln Arg Tyr Pro Arg
            260                 265                 270

Thr Lys Val Glu Glu Lys Glu Ala Ser Asp Thr Gly Gly Glu Glu Pro
        275                 280                 285

Glu Lys Glu Glu Glu Asp Leu Tyr Tyr Gly Leu Pro Asp Gly Ala Gly
    290                 295                 300

Asp Leu Leu Pro Asp Lys Glu Leu Gly Phe Glu Pro Asp Thr Gln Gly
305                 310                 315                 320

<210> SEQ ID NO 11
<211> LENGTH: 1396
<212> TYPE: DNA
<213> ORGANISM: Homo sapiens

<400> SEQUENCE: 11
gagagggcaa ggagtaaagg tggctgggtg tgggtccgtt gaagcgagcc gcctccagcc    60
ctgttgaact ggtgggccca gggactggag cgggattgaa agggatcttg ctctcccttg   120
aagcctcgag ttgcagcgat ttcagtgtct tctctccctg tgtaagcctg tctgggtgtt   180
taggctgaac tacagccacc ccctctcccg ggggtgtgca ggccagggac tggccaggca   240
gccatggctg acgagaagac cttcctgatc ggcttcattg tgctggggct tttcctgctg   300
gccctcggta cgttcctcat gagccatgat cggccccagg tctacggcac cttctatgcc   360
atgggcagcg tcatggtgat cgggggcatc atctggagca tgtgccagtg ctaccccaag   420
atcaccttcg tccctgctga ctctgacttt caaggcatcc tctccccaaa ggccatgggc   480
ctgctggaga tgggcttgc tgccgagatg aagagcccca gtccccagcc gcctatgta   540 aggctgtggg aggaagccgc ctatgaccag agcctgcctg acttcagcca catccagatg   600
aaagtcatga gctacagtga ggaccaccgc tccttgctgg cccctgagat ggggcagccg   660
aagctgggaa ccagtgatgg aggagaaggt ggccctggcg acgttcaggc tggatggag   720 gctgccgtgg tcatccacaa gggctcagac gagagtgaag gggaaagacg cctaactcag   780
agctggcccg gccccctggc ctgtccccag ggccctgccc cttggcttc cttccaagat   840 gacctggaca tggactccag tgaaggcagc agccccaatg catctccaca tgacagggag   900
gaagcttgtt ccccacaaca ggaacctcag ggctgcaggt gccgctgga ccgcttccaa   960
```

```
gactttgccc tgattgatgc cccaacgttg gaggatgagc cccaagaggg gcagcagtgg    1020
gaaatagccc tgcccaacaa ctggcagcgg tacccaagga caaaggtgga ggagaaggag    1080
gcttcggaca caggtgggga ggaacctgag aaggaagagg aagacctgta ctatgggctg    1140
ccagatggag ccggggacct cctcccggac aaggagctgg gttttgagcc tgacacccaa    1200
ggctgagatg tttgtgctcc gtagcttttta gtctggaact gctgctgacc cctgtgtgac    1260
atcacagggc ctcagtttcc ctatttgcaa aatgggatga tatggaggtt caatgagatg    1320
gtggcatttt gagaatggta agaaatacc cagggagggg atgatgccta aaaaaaaaa     1380 aaaaaaaaaa aaaaaa                                                    1396
```

<210> SEQ ID NO 12
<211> LENGTH: 320
<212> TYPE: PRT
<213> ORGANISM: Homo sapiens

<400> SEQUENCE: 12

```
Met Ala Asp Glu Lys Thr Phe Leu Ile Gly Phe Ile Val Leu Gly Leu
1               5                   10                  15

Phe Leu Leu Ala Leu Gly Thr Phe Leu Met Ser His Asp Arg Pro Gln
            20                  25                  30

Val Tyr Gly Thr Phe Tyr Ala Met Gly Ser Val Met Val Ile Gly Gly
        35                  40                  45

Ile Ile Trp Ser Met Cys Gln Cys Tyr Pro Lys Ile Thr Phe Val Pro
    50                  55                  60

Ala Asp Ser Asp Phe Gln Gly Ile Leu Ser Pro Lys Ala Met Gly Leu
65                  70                  75                  80

Leu Glu Asn Gly Leu Ala Ala Glu Met Lys Ser Pro Ser Pro Gln Pro
                85                  90                  95

Pro Tyr Val Arg Leu Trp Glu Glu Ala Ala Tyr Asp Gln Ser Leu Pro
            100                 105                 110

Asp Phe Ser His Ile Gln Met Lys Val Met Ser Tyr Ser Glu Asp His
        115                 120                 125

Arg Ser Leu Leu Ala Pro Glu Met Gly Gln Pro Lys Leu Gly Thr Ser
    130                 135                 140

Asp Gly Gly Glu Gly Gly Pro Gly Asp Val Gln Ala Trp Met Glu Ala
145                 150                 155                 160

Ala Val Val Ile His Lys Gly Ser Asp Glu Ser Glu Gly Glu Arg Arg
                165                 170                 175

Leu Thr Gln Ser Trp Pro Gly Pro Leu Ala Cys Pro Gln Gly Pro Ala
            180                 185                 190

Pro Leu Ala Ser Phe Gln Asp Asp Leu Asp Met Asp Ser Ser Glu Gly
        195                 200                 205

Ser Ser Pro Asn Ala Ser Pro His Asp Arg Glu Glu Ala Cys Ser Pro
    210                 215                 220

Gln Gln Glu Pro Gln Gly Cys Arg Cys Pro Leu Asp Arg Phe Gln Asp
225                 230                 235                 240

Phe Ala Leu Ile Asp Ala Pro Thr Leu Glu Asp Glu Pro Gln Glu Gly
                245                 250                 255

Gln Gln Trp Glu Ile Ala Leu Pro Asn Asn Trp Gln Arg Tyr Pro Arg
            260                 265                 270

Thr Lys Val Glu Glu Lys Glu Ala Ser Asp Thr Gly Gly Glu Glu Pro
        275                 280                 285

Glu Lys Glu Glu Glu Asp Leu Tyr Tyr Gly Leu Pro Asp Gly Ala Gly
```

```
                  290                 295                 300
Asp Leu Leu Pro Asp Lys Glu Leu Gly Phe Glu Pro Asp Thr Gln Gly
305                 310                 315                 320
```

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gagcagagag aagaccgagt c                                         21

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
tgtcttctct ccctgtgtaa gc                                        22

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
tgcctaactc acagaattga gag                                       23

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
acagaggctg tctctccttt g                                         21

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
ctctcctttt taaccttga actg                                       24

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
gaccacatac ccaaagcaaa c                                         21

<210> SEQ ID NO 19

-continued

```
<211> LENGTH: 21
<212> TYPE: DNA
<213> ORGANISM: Artificial Sequence
<220> FEATURE:
<223> OTHER INFORMATION: Synthetic

<400> SEQUENCE: 19
ccattttgca gatagggaaa c                                          21

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
cgggaaggtg gattatccta c                                          21

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
atggcacagc caagaatgct ccag                                       24

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
atctgggcac aggcgatctc aaggt                                      25

<210> SEQ ID NO 23
<211> LENGTH: 81
<212> TYPE: PRT
<213> ORGANISM: Mus musculus

<400> SEQUENCE: 23

Ser Val Leu Ser Ala Ser Val Thr Gly Pro Pro Leu Thr Ala Ser Val
1               5                   10                  15

Arg Glu Arg Thr Ala Pro Val Arg Asn Lys Ser His Ser Ser Ser Val
            20                  25                  30

Gly Ser His Val Gly Leu Gln Pro Asn Arg Asp Pro His Arg Val Trp
        35                  40                  45

Ala Ser Gly Ser Asp Thr Ser Thr Val Leu Asp Ala Arg Ala Pro Lys
    50                  55                  60

Gln Trp Ser Leu Met Gly Thr Val Gln Arg Ala Gln Ser Pro Asn Pro
65                  70                  75                  80

Ile

<210> SEQ ID NO 24
<211> LENGTH: 15
<212> TYPE: PRT
<213> ORGANISM: Murray Valley encephalitis virus

<400> SEQUENCE: 24
```

```
Val Pro Ala Asp Ser Asp Phe Gln Gly Ile Leu Ser Pro Lys Ala
1               5                   10                  15
```

<210> SEQ ID NO 25
<211> LENGTH: 14
<212> TYPE: PRT
<213> ORGANISM: Murray Valley encephalitis virus

<400> SEQUENCE: 25

```
Pro Glu Gln Glu Glu Asp Leu Tyr Tyr Gly Leu Pro Asp
1               5                   10
```

<210> SEQ ID NO 26
<211> LENGTH: 15
<212> TYPE: PRT
<213> ORGANISM: Murray Valley encephalitis virus

<400> SEQUENCE: 26

```
Leu Leu Pro Asp Lys Glu Leu Gly Phe Glu Pro Asp Ile Gln Gly
1               5                   10                  15
```

<210> SEQ ID NO 27
<211> LENGTH: 13
<212> TYPE: PRT
<213> ORGANISM: Homo sapiens

<400> SEQUENCE: 27

```
Ala Leu Thr Ala Pro Pro Pro Ala Tyr Ala Thr Leu Gly
1               5                   10
```

<210> SEQ ID NO 28
<211> LENGTH: 13
<212> TYPE: PRT
<213> ORGANISM: Homo sapiens

<400> SEQUENCE: 28

```
Ile Pro Gly Thr Pro Pro Pro Asn Tyr Asp Ser Leu Arg
1               5                   10
```

<210> SEQ ID NO 29
<211> LENGTH: 13
<212> TYPE: PRT
<213> ORGANISM: Homo sapiens

<400> SEQUENCE: 29

```
Val Pro Gly Thr Pro Pro Pro Lys Tyr Asn Thr Leu Arg
1               5                   10
```

<210> SEQ ID NO 30
<211> LENGTH: 13
<212> TYPE: PRT
<213> ORGANISM: Homo sapiens

<400> SEQUENCE: 30

```
Glu His Ser Pro Pro Leu Pro Pro Tyr Thr Pro Pro Thr
1               5                   10
```

<210> SEQ ID NO 31
<211> LENGTH: 13
<212> TYPE: PRT
<213> ORGANISM: Homo sapiens

<400> SEQUENCE: 31

```
Lys Ser Pro Ser Pro Gln Pro Pro Tyr Val Arg Leu Trp
1               5                   10
```

```
<210> SEQ ID NO 32
<211> LENGTH: 2
<212> TYPE: PRT
<213> ORGANISM: Homo sapiens

<400> SEQUENCE: 32

Met Ala
1

<210> SEQ ID NO 33
<211> LENGTH: 2
<212> TYPE: PRT
<213> ORGANISM: Homo sapiens

<400> SEQUENCE: 33

Leu Ala
1

<210> SEQ ID NO 34
<211> LENGTH: 12
<212> TYPE: DNA
<213> ORGANISM: Homo sapiens

<400> SEQUENCE: 34
gcagccatgg ct                                                      12

<210> SEQ ID NO 35
<211> LENGTH: 12
<212> TYPE: DNA
<213> ORGANISM: Homo sapiens

<400> SEQUENCE: 35
gcagccttgg ct                                                      12

<210> SEQ ID NO 36
<211> LENGTH: 4
<212> TYPE: PRT
<213> ORGANISM: Homo sapiens

<400> SEQUENCE: 36

Phe Arg Ile Gly
1

<210> SEQ ID NO 37
<211> LENGTH: 4
<212> TYPE: PRT
<213> ORGANISM: Homo sapiens

<400> SEQUENCE: 37

Phe Trp Ile Gly
1

<210> SEQ ID NO 38
<211> LENGTH: 12
<212> TYPE: DNA
<213> ORGANISM: Homo sapiens

<400> SEQUENCE: 38
ttccggatcg gc                                                      12

<210> SEQ ID NO 39
<211> LENGTH: 12
<212> TYPE: DNA
```

```
<213> ORGANISM: Homo sapiens

<400> SEQUENCE: 39
ttctggatcg gc                                                          12

<210> SEQ ID NO 40
<211> LENGTH: 76
<212> TYPE: DNA
<213> ORGANISM: Homo sapiens

<400> SEQUENCE: 40
atctggagca tgtgccagtg ctaccccaag gtaggtggta gtggggctgg gtggggccag      60
gtcagctggg gccagg                                                      76

<210> SEQ ID NO 41
<211> LENGTH: 17
<212> TYPE: DNA
<213> ORGANISM: Homo sapiens

<400> SEQUENCE: 41
atctggagcg tggggcc                                                     17

<210> SEQ ID NO 42
<211> LENGTH: 33
<212> TYPE: DNA
<213> ORGANISM: Homo sapiens

<400> SEQUENCE: 42
gggttaggga tgatctctgc tttgcttggg gaa                                   33

<210> SEQ ID NO 43
<211> LENGTH: 33
<212> TYPE: DNA
<213> ORGANISM: Homo sapiens

<400> SEQUENCE: 43
gggttaggga tgatctcttg cccaagctgt tct                                   33

<210> SEQ ID NO 44
<211> LENGTH: 33
<212> TYPE: DNA
<213> ORGANISM: Homo sapiens

<400> SEQUENCE: 44
tcttgcggct cacactcttg cccaagctgt tct                                   33

<210> SEQ ID NO 45
<211> LENGTH: 11
<212> TYPE: PRT
<213> ORGANISM: Homo sapiens

<400> SEQUENCE: 45

Met Ala Asp Glu Lys Thr Phe Arg Ile Gly Phe
1               5                   10

<210> SEQ ID NO 46
<211> LENGTH: 11
<212> TYPE: PRT
<213> ORGANISM: Homo sapiens

<400> SEQUENCE: 46

Ile Ala Asp Glu Lys Thr Phe Arg Ile Ser Phe
1               5                   10
```

```
<210> SEQ ID NO 47
<211> LENGTH: 33
<212> TYPE: DNA
<213> ORGANISM: Homo sapiens

<400> SEQUENCE: 47
atggctgacg agaagacctt ccggatcggc ttc                           33

<210> SEQ ID NO 48
<211> LENGTH: 33
<212> TYPE: DNA
<213> ORGANISM: Homo sapiens

<400> SEQUENCE: 48
atrgctgacg agaagacctt ccggatcrgc ttc                           33

<210> SEQ ID NO 49
<211> LENGTH: 4
<212> TYPE: PRT
<213> ORGANISM: Homo sapiens

<400> SEQUENCE: 49

Phe Arg Ile Gly
1

<210> SEQ ID NO 50
<211> LENGTH: 4
<212> TYPE: PRT
<213> ORGANISM: Homo sapiens

<400> SEQUENCE: 50

Phe Leu Ile Gly
1

<210> SEQ ID NO 51
<211> LENGTH: 12
<212> TYPE: DNA
<213> ORGANISM: Homo sapiens

<400> SEQUENCE: 51
ttccggatcg gc                                                  12

<210> SEQ ID NO 52
<211> LENGTH: 12
<212> TYPE: DNA
<213> ORGANISM: Homo sapiens

<400> SEQUENCE: 52
ttcctgatcg gc                                                  12
```